(12) United States Patent
Scheller et al.

(10) Patent No.: US 9,452,012 B2
(45) Date of Patent: *Sep. 27, 2016

(54) BIPOLAR FORCEPS

(71) Applicant: Kogent Surgical, LLC, Chesterfield, MO (US)

(72) Inventors: Gregg D Scheller, Wildwood, MO (US); John M Schallert, Lake St. Louis, MO (US)

(73) Assignee: Kogent Surgical, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/694,659

(22) Filed: Apr. 23, 2015

(65) Prior Publication Data

US 2015/0223875 A1 Aug. 13, 2015

Related U.S. Application Data

(63) Continuation of application No. 13/742,120, filed on Jan. 15, 2013, now Pat. No. 9,044,242.

(51) Int. Cl.
*A61B 18/14* (2006.01)
*A61B 17/29* (2006.01)
*A61B 18/00* (2006.01)

(52) U.S. Cl.
CPC ....... *A61B 18/1445* (2013.01); *A61B 17/2909* (2013.01); *A61B 18/1442* (2013.01); *A61B 2018/0063* (2013.01); *A61B 2018/00083* (2013.01); *A61B 2018/00107* (2013.01); *A61B 2018/00589* (2013.01); *A61B 2018/00595* (2013.01)

(58) Field of Classification Search
CPC .......... A61B 18/1442; A61B 17/2909; A61B 18/1445
See application file for complete search history.

(56) References Cited

U.S. PATENT DOCUMENTS

| 3,100,489 A | 8/1963 | Bagley |
| 5,647,871 A | 7/1997 | Levine et al. |
| 5,674,220 A | 10/1997 | Fox et al. |
| 6,050,996 A | 4/2000 | Schmaltz et al. |
| 6,231,574 B1 * | 5/2001 | Posthuma .......... A61B 18/1442 606/51 |

(Continued)

FOREIGN PATENT DOCUMENTS

EP 1709923 A2 10/2006

OTHER PUBLICATIONS

Sutter; "SuperGliss non-stick bipolar forceps" brochure, 2012.

(Continued)

*Primary Examiner* — Catherine Voorhees
(74) *Attorney, Agent, or Firm* — Kevin P. Rollins

(57) ABSTRACT

A bipolar forceps may include a first forceps arm having a first forceps arm aperture, a first forceps jaw, and a first forceps arm conductor tip; a second forceps arm having a first forceps arm aperture, a second forceps jaw, and a second forceps arm conductor tip; and an input conductor isolation mechanism having a first forceps arm housing and a second forceps arm housing. The first forceps arm may be disposed in the first forceps arm housing and the second forceps arm may be disposed in the second forceps arm housing. An application of a force to a lateral portion of the forceps arms may be configured to close the forceps jaws. A reduction of a force applied to a lateral portion of the forceps arms may be configured to open the forceps jaws.

20 Claims, 15 Drawing Sheets

(56) References Cited

U.S. PATENT DOCUMENTS

| | | |
|---|---|---|
| 6,293,946 B1 | 9/2001 | Thorne |
| 6,482,205 B1 | 11/2002 | Bonnet |
| 6,679,881 B1 | 1/2004 | Bybee |
| 6,749,610 B2 | 6/2004 | Kirwan, Jr. et al. |
| 6,767,348 B2 | 7/2004 | Nakada et al. |
| 6,860,882 B2 | 3/2005 | Battles et al. |
| 7,122,035 B2 | 10/2006 | Canady |
| 7,150,097 B2 | 12/2006 | Sremcich et al. |
| D559,984 S * | 1/2008 | Scheller ................... D24/143 |
| 7,736,361 B2 | 6/2010 | Palanker et al. |
| 7,867,230 B2 * | 1/2011 | Asahara ............. A61B 18/1442 606/51 |
| 7,963,965 B2 | 6/2011 | Buysse et al. |
| 8,048,107 B2 | 11/2011 | Chen |
| 8,083,735 B2 | 12/2011 | Morris |
| 8,108,994 B2 | 2/2012 | Ariola, Jr. et al. |
| 8,192,433 B2 | 6/2012 | Johnson et al. |
| 8,211,105 B2 | 7/2012 | Buysse et al. |
| 8,469,956 B2 | 6/2013 | McKenna et al. |
| 9,044,242 B2 * | 6/2015 | Scheller ............. A61B 17/2909 |
| 2003/0069571 A1 * | 4/2003 | Treat .................... A61B 18/085 606/29 |
| 2005/0107784 A1 | 5/2005 | Moses et al. |
| 2006/0004356 A1 * | 1/2006 | Bilski ................ A61B 18/1442 606/51 |
| 2006/0217709 A1 | 9/2006 | Couture et al. |
| 2008/0200914 A1 * | 8/2008 | Hanlon .............. A61B 18/1442 606/48 |
| 2012/0004653 A1 | 1/2012 | Butsch |
| 2013/0066317 A1 * | 3/2013 | Evans .................. A61B 18/042 606/48 |
| 2014/0128909 A1 * | 5/2014 | Scheller ............. A61B 17/2909 606/207 |
| 2014/0194870 A1 * | 7/2014 | Hanlon .............. A61B 18/1442 606/41 |

OTHER PUBLICATIONS

Stingray Surgical Products, Inc. brochure, 2010.
Olsen Medical; "Single Use Bipolar Forceps" brochure, 2008.
AESCULAP brochure, 2012.
Sutter; "Bipolar Forceps" brochure, 2012.
Manuel Dujovny et al., Bipolar Jeweler's Forceps With Automatic Irrigation, for Coagulation in Microsurgery, Plastic and Reconstructive Surgery, 585-587, Nov. 1975.
Ananth K. Vellimana et al., Current Technological Advances of Bipolar Coagulation, Operative Neurosurgery, No. 1, vol. 64, 11-19, Mar. 2009.
Ebonia W. Elliott-Lewis et al., Evaluation of New Bipolar Coagulation Forceps in a Thermal Damage Assessment, Operative Neurosurgery, No. 6, vol. 65, 1182-1187, Dec. 2009.
Manuel Dujovny et al., Bipolar Coagulation in Neurosurgery, Surg. Neurol. 1998; 49:328-32.
Leonard I. Malis, Electrosurgery and Bipolar Technology, Operative Neurosurgery, No. 1, vol. 58, 1-12, Feb. 2006.
Ebonia W. Elliott-Lewis et al., Thermal Damage Assessment of Novel Bipolar Forceps in a Sheep Model of Spinal Surgery, Neurosurgery 67:166-172, 2010.
Soring Product Catalog, Sep. 2011.

* cited by examiner

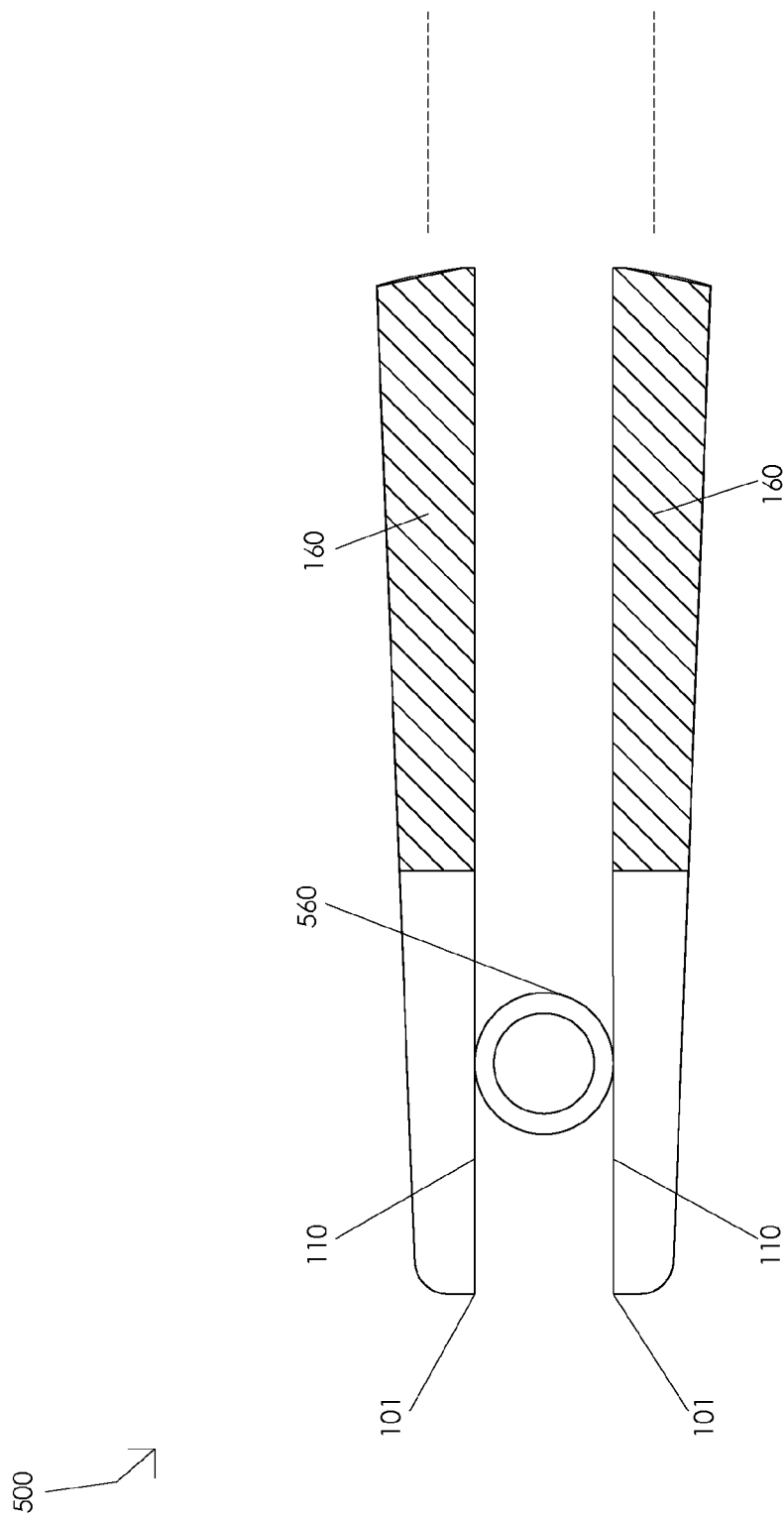

BIPOLAR FORCEPS

CROSS-REFERENCE TO RELATED APPLICATIONS

This Application is a continuation of prior application Ser. No. 13/742,120, filed Jan. 15, 2013.

FIELD OF THE INVENTION

The present disclosure relates to a medical device, and, more particularly, to a surgical instrument.

BACKGROUND OF THE INVENTION

A variety of complete surgical procedures and portions of surgical procedures may be performed with bipolar forceps, e.g., bipolar forceps are commonly used in dermatological, gynecological, cardiac, plastic, ocular, spinal, maxillofacial, orthopedic, urological, and general surgical procedures. Bipolar forceps are also used in neurosurgical procedures; however, the use of bipolar forceps in neurosurgical procedures presents unique risks to patients if the surgeon is unable to both visually and tactilely confirm that an electrosurgical procedure is being performed as intended. Accordingly, there is a need for a bipolar forceps that allows a surgeon to both visually and tactilely confirm that an electrosurgical procedure is being performed as intended.

BRIEF SUMMARY OF THE INVENTION

The present disclosure presents a bipolar forceps. Illustratively, a bipolar forceps may comprise a first forceps arm having a first forceps arm aperture, a first forceps jaw, and a first forceps arm conductor tip; a second forceps arm having a first forceps arm aperture, a second forceps jaw, and a second forceps arm conductor tip; and an input conductor isolation mechanism having a first forceps arm housing and a second forceps arm housing. In one or more embodiments, the first forceps arm may be disposed in the first forceps arm housing and the second forceps arm may be disposed in the second forceps arm housing. Illustratively, an application of a force to a lateral portion of the forceps arms may be configured to close the forceps jaws. In one or more embodiments, a reduction of a force applied to a lateral portion of the forceps arms may be configured to open the forceps jaws.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 5A, 5B, and 5C are schematic diagrams illustrating a uniform compression of a vessel.

DETAILED DESCRIPTION OF AN ILLUSTRATIVE EMBODIMENT

Figure 1:
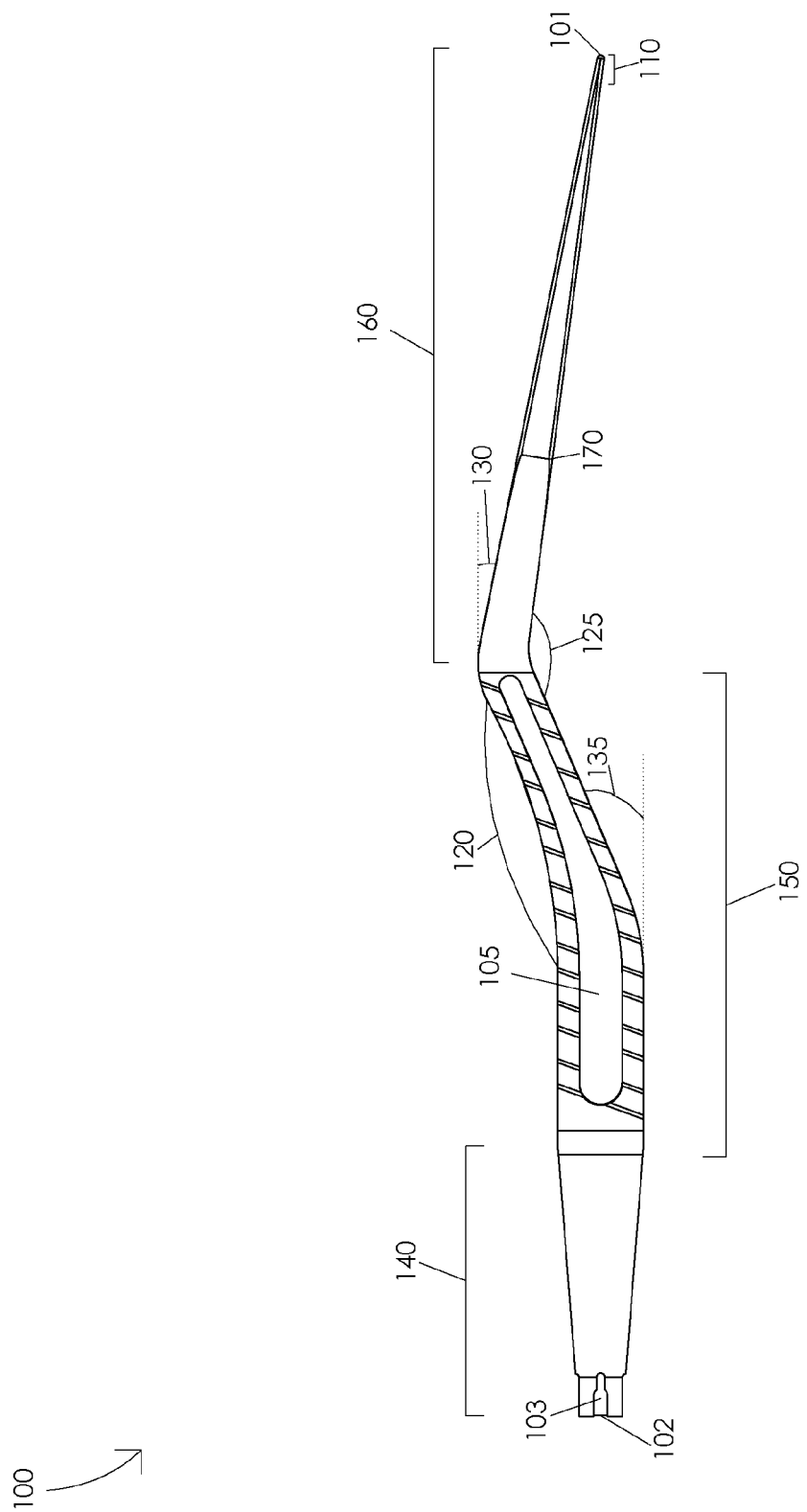
FIG. 1 is a schematic diagram illustrating a side view of a forceps arm.

FIG. 1 is a schematic diagram illustrating a side view of a forceps arm 100. Illustratively, a forceps arm 100 may comprise an input conductor housing 103, a forceps arm aperture 105, a conductor tip 110, a forceps arm superior incline angle 120, a forceps arm inferior decline angle 125, a forceps arm superior decline angle 130, a forceps arm inferior incline angle 135, a socket interface 140, a forceps arm grip 150, a forceps jaw 160, and a forceps jaw taper interface 170. In one or more embodiments, forceps arm 100 may be may be manufactured from any suitable material, e.g., polymers, metals, metal alloys, etc., or from any combination of suitable materials. Illustratively, forceps arm 100 may be manufactured from an electrically conductive material, e.g., metal, graphite, conductive polymers, etc. In one or more embodiments, forceps arm 100 may be manufactured from an electrically conductive metal, e.g., silver, copper, gold, aluminum, etc. Illustratively, forceps arm 100 may be manufactured from an electrically conductive metal alloy, e.g., a silver alloy, a copper alloy, a gold alloy, an aluminum alloy, stainless steel, etc.

In one or more embodiments, forceps arm 100 may be manufactured from a material having an electrical conductivity in a range of $30.0 \times 10^6$ to $40.0 \times 10^6$ Siemens per meter at a temperature of 20.0° C., e.g., forceps arm 100 may be manufactured from a material having an electrical conductivity of $35.5 \times 10^6$ Siemens per meter at a temperature of 20.0° C. Illustratively, forceps arm 100 may be manufactured from a material having an electrical conductivity of less than $30.0 \times 10^6$ Siemens per meter or greater than $40.0 \times 10^6$ Siemens per meter at a temperature of 20.0° C. In one or more embodiments, forceps arm 100 may be manufactured from a material having a thermal conductivity in a range of 180.0 to 250.0 Watts per meter Kelvin at a temperature of 20.0° C., e.g., forceps arm 100 may be manufactured from a material having a thermal conductivity of 204.0 Watts per meter Kelvin at a temperature of 20.0° C. Illustratively, forceps arm 100 may be manufactured from a material having a thermal conductivity of less than 180.0 Watts per meter Kelvin or greater than 250.0 Watts per meter Kelvin at a temperature of 20.0° C. In one or more embodiments, forceps arm 100 may be manufactured from a material having an electrical conductivity in a range of $30.0 \times 10^6$ to $40.0 \times 10^6$ Siemens per meter and a thermal conductivity in a range of 180.0 to 250.0 Watts per meter Kelvin at a temperature of 20.0° C., e.g., forceps arm 100 may be manufactured from a material having an electrical conductivity of $35.5 \times 10^6$ Siemens per meter and a thermal conductivity of 204.0 Watts per meter Kelvin at a temperature of 20.0° C.

Illustratively, forceps arm 100 may have a density in a range of 0.025 to 0.045 pounds per cubic inch, e.g., forceps arm 100 may have a density of 0.036 pounds per cubic inch. In one or more embodiments, forceps arm 100 may have a density less than 0.025 pounds per cubic inch or greater than 0.045 pounds per cubic inch. For example, forceps arm 100 may have a density of 0.0975 pounds per cubic inch. Illustratively, forceps arm 100 may have a mass in a range of 0.01 to 0.025 pounds, e.g., forceps arm 100 may have a mass of 0.017 pounds. In one or more embodiments, forceps arm 100 may have a mass less than 0.01 pounds or greater than 0.025 pounds. Illustratively, forceps arm 100 may have a volume in a range of 0.12 to 0.23 cubic inches, e.g., forceps arm 100 may have a volume of 0.177 cubic inches. In one or more embodiments, forceps arm 100 may have a volume less than 0.12 cubic inches or greater than 0.23 cubic inches. Illustratively, forceps arm aperture 105 may be configured to reduce a stiffness of forceps arm 100. In one or more embodiments, forceps arm aperture 105 may be configured to increase a flexibility of forceps arm 100.

Illustratively, forceps arm aperture 105 may be configured to reduce a mass of forceps arm 100. In one or more embodiments, forceps arm aperture 105 may be configured to reduce a mass of forceps arm 100 by an avoided mass in a range of 0.005 to 0.012 pounds, e.g., forceps arm aperture 105 may be configured to reduce a mass of forceps arm 100 by an avoided mass of 0.00975 pounds. Illustratively, forceps arm aperture 105 may be configured to reduce a mass of forceps arm 100 by an avoided mass less than 0.005 pounds or greater than 0.012 pounds. In one or more embodiments, forceps arm aperture 105 may have an aperture area in a range of 0.3 to 0.65 square inches, e.g., forceps arm aperture 105 may have an aperture area of 0.485 square inches. Illustratively, forceps arm aperture 105 may have an aperture area less than 0.3 square inches or greater than 0.65 square inches. In one or more embodiments, forceps arm aperture 105 may have an aperture perimeter length in a range of 4.0 to 7.0 inches, e.g., forceps arm aperture 105 may have an aperture perimeter length of 5.43 inches. Illustratively, forceps arm aperture 105 may have an aperture perimeter length less than 4.0 inches or greater than 7.0 inches.

In one or more embodiments, forceps arm aperture 105 may be configured to decrease a thermal conductivity of forceps arm grip 150. Illustratively, forceps arm aperture 105 may be configured to decrease an electrical conductivity of forceps arm grip 150. In one or more embodiments, forceps arm aperture 105 may be configured to decrease a thermal conductivity and to decrease an electrical conductivity of forceps arm grip 150. Illustratively, forceps arm aperture 105 may be configured to reduce a probability that forceps arm grip 150 may reach a temperature of 48.89° C. during a surgical procedure. In one or more embodiments, forceps arm aperture 105 may be configured to reduce a probability that forceps arm grip 150 may reach a temperature of 48.89° C. during a surgical procedure, e.g., by decreasing a thermal conductivity of forceps arm grip 150. Illustratively, forceps arm aperture 105 may be configured to reduce a probability that forceps arm grip 150 may reach a temperature of 48.89° C. during a surgical procedure, e.g., by decreasing an electrical conductivity of forceps arm grip 150. In one or more embodiments, forceps arm aperture 105 may be configured to reduce a probability that forceps arm grip 150 may reach a temperature of 48.89° C. during a surgical procedure, e.g., by decreasing a thermal conductivity and an electrical conductivity of forceps arm grip 150.

Illustratively, forceps arm 100 may have a surface area in a range of 4.5 to 7.5 square inches, e.g., forceps arm 100 may have a surface area of 6.045 square inches. In one or more embodiments, forceps arm 100 may have a surface area less than 4.5 square inches or greater than 7.5 square inches. Illustratively, conductor tip 110 may have a surface area in a range of 0.02 to 0.05 square inches, e.g., conductor tip 110 may have a surface area of 0.035 square inches. In one or more embodiments, conductor tip 110 may have a surface area less than 0.02 square inches or greater than 0.05 square inches. Illustratively, a ratio of forceps arm 100 surface area to conductor tip 110 surface area may be in a range of 150.0 to 225.0, e.g., a ratio of forceps arm 100 surface area to conductor tip 110 surface area may be 172.7. In one or more embodiments, a ratio of forceps arm 100 surface area to conductor tip 110 surface area may be less than 150.0 or greater than 225.0.

Illustratively, conductor tip 110 may be configured to prevent tissue from sticking to conductor tip 110. In one or more embodiments, conductor tip 110 may comprise an evenly polished material configured to prevent tissue sticking. Illustratively, conductor tip 110 may have a length in a range of 0.22 to 0.3 inches, e.g., conductor tip 110 may have a length of 0.26 inches. In one or more embodiments, conductor tip 110 may have a length less than 0.22 inches or greater than 0.3 inches. Illustratively, conductor tip 110 may have a width in a range of 0.03 to 0.05 inches, e.g., conductor tip 110 may have a width of 0.04 inches. In one or more embodiments, conductor tip 110 may have a width less than 0.03 inches or greater than 0.05 inches. Illustratively, a geometry of forceps jaw 160 may comprise a tapered portion, e.g., a tapered portion from forceps jaw taper interface 170 to forceps arm distal end 101. In one or more embodiments, forceps jaw 160 may comprise a tapered portion having a tapered angle in a range of 3.0 to 4.5 degrees, e.g., forceps jaw 160 may comprise a tapered portion having a tapered angle of 3.72 degrees. Illustratively, forceps jaw 160 may comprise a tapered portion having a tapered angle of less than 3.0 degrees or greater than 4.5 degrees.

Illustratively, forceps arm 100 may comprise a material having a modulus of elasticity in a range of $9.0 \times 10^6$ to $11.0 \times 10^6$ pounds per square inch, e.g., forceps arm 100 may comprise a material having a modulus of elasticity of $10.0 \times 10^6$ pounds per square inch. In one or more embodiments, forceps arm 100 may comprise a material having a modulus of elasticity less than $9.0 \times 10^6$ pounds per square inch or greater than $11.0 \times 10^6$ pounds per square inch. Illustratively, forceps arm 100 may comprise a material having a shear modulus in a range of $3.5 \times 10^6$ to $4.5 \times 10^6$ pounds per square inch, e.g., forceps arm 100 may comprise a material having a shear modulus of $3.77 \times 10^6$ pounds per square inch. In one or more embodiments, forceps arm 100 may comprise a material having a shear modulus less than $3.5 \times 10^6$ pounds per square inch or greater than $4.5 \times 10^6$ pounds per square inch.

Illustratively, forceps arm superior incline angle 120 may comprise any angle greater than 90.0 degrees. In one or more embodiments, forceps arm superior incline angle 120 may comprise any angle in a range of 150.0 to 170.0 degrees, e.g., forceps arm superior incline angle 120 may comprise a 160.31 degree angle. Illustratively, forceps arm superior incline angle 120 may comprise an angle less than 150.0 degrees or greater than 170.0 degrees. In one or more embodiments, forceps arm inferior decline angle 125 may comprise any angle greater than 90.0 degrees. Illustratively, forceps arm inferior decline angle 125 may comprise any angle in a range of 140.0 to 160.0 degrees, e.g., forceps arm inferior decline angle 125 may comprise a 149.56 degree angle. In one or more embodiments, forceps arm inferior decline angle 125 may comprise an angle less than 140.0 degrees or greater than 160.0 degrees. Illustratively, forceps arm inferior decline angle 125 may comprise any angle less than forceps arm superior incline angle 120, e.g., forceps arm inferior decline angle 125 may comprise an angle in a range of 5.0 to 15.0 degrees less than forceps arm superior incline angle 120. In one or more embodiments, forceps arm inferior decline angle 125 may comprise an angle less than 5.0 degrees or greater than 15.0 degrees less than forceps arm superior incline angle 120.

Illustratively, forceps arm superior decline angle 130 may comprise any angle less than 90.0 degrees. In one or more embodiments, forceps arm superior decline angle 130 may comprise any angle in a range of 5.0 to 15.0 degrees, e.g., forceps arm superior decline angle 130 may comprise an 11.3 degree angle. Illustratively, forceps arm superior decline angle 130 may comprise an angle less than 5.0 degrees or greater than 15.0 degrees. In one or more embodiments, forceps arm inferior incline angle 135 may comprise any angle less than 90.0 degrees. Illustratively, forceps arm inferior incline angle 135 may comprise any angle in a range of 15.0 to 30.0 degrees, e.g., forceps arm inferior incline angle 135 may comprise a 23.08 degree angle. In one or more embodiments, forceps arm inferior incline angle 135 may comprise an angle less than 15.0 degrees or greater than 30.0 degrees. Illustratively, forceps arm inferior incline angle 135 may comprise any angle greater than forceps arm superior decline angle 130, e.g., forceps arm inferior incline angle 135 may comprise an angle in a range of 5.0 to 15.0 degrees greater than forceps arm superior decline angle 130. In one or more embodiments, forceps arm inferior incline angle 135 may comprise an angle less than 5.0 degrees or greater than 15.0 degrees greater than forceps arm superior decline angle 130.

Figure 2:
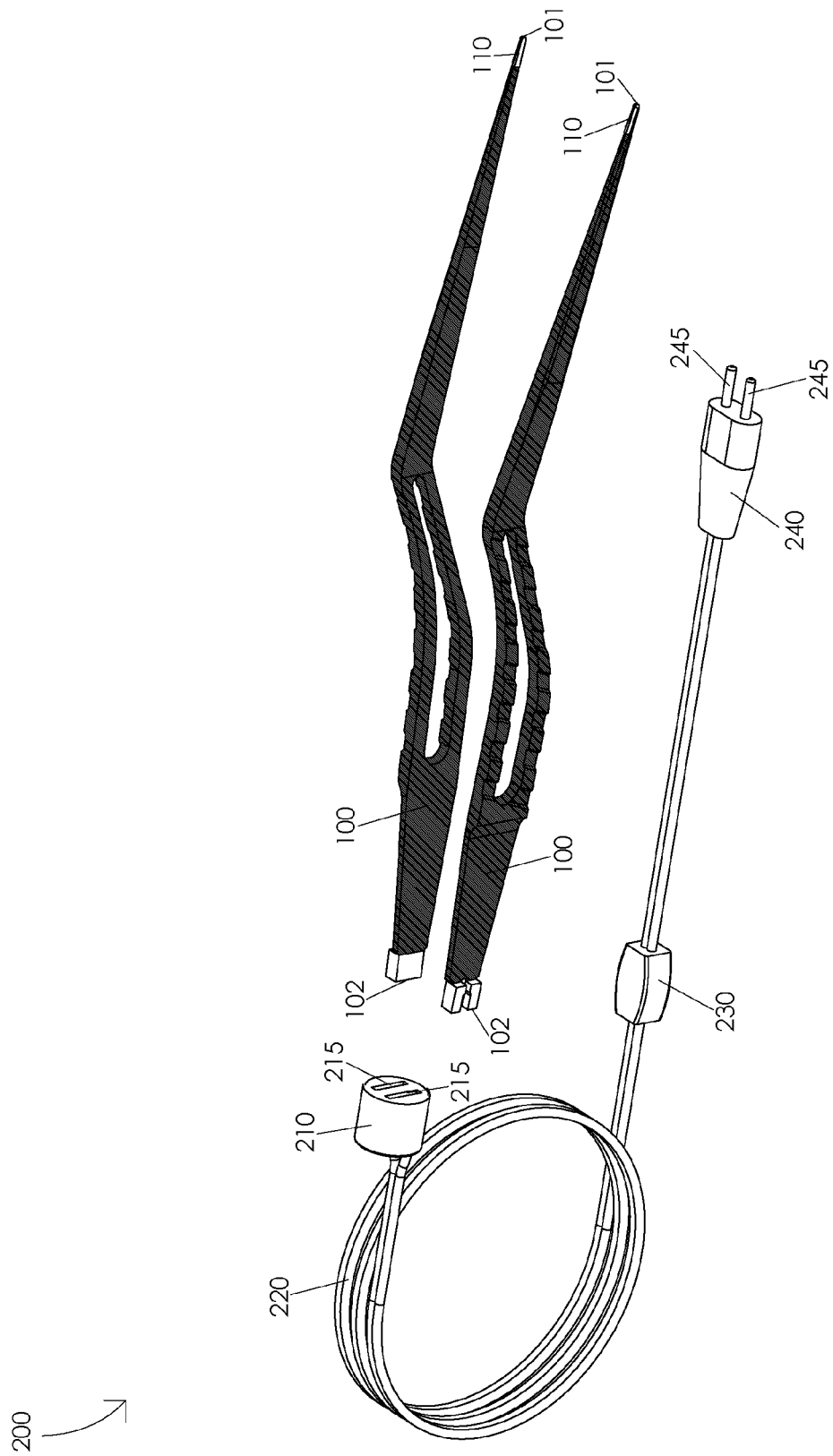
FIG. 2 is a schematic diagram illustrating an exploded view of a bipolar forceps assembly.

FIG. 2 is a schematic diagram illustrating an exploded view of a bipolar forceps assembly 200. In one or more embodiments, a bipolar forceps assembly 200 may comprise a pair of forceps arms 100, an input conductor isolation mechanism 210, a bipolar cord 220, a bipolar cord separation control 230, and an electrosurgical generator adaptor 240. Illustratively, a portion of each forceps arm 100 may be coated with a material having a high electrical resistivity, e.g., a portion of each forceps arm 100 may be coated with an electrical insulator material. In one or more embodiments, input conductor housings 103 and conductor tips 110 may not be coated with a material, e.g., input conductor housings 103 and conductor tips 110 may comprise electrical leads. Illustratively, a portion of each forceps arm 100 may be coated with a thermoplastic material, e.g., a portion of each forceps arm 100 may be coated with nylon. In one or more embodiments, a portion of each forceps arm 100 may be coated with a fluoropolymer, e.g., a portion of each forceps arm 100 may be coated with polyvinylidene fluoride. Illustratively, a portion of each forceps arm 100 may be coated with a material having an electrical conductivity less than $1.0 \times 10^{-8}$ Siemens per meter at a temperature of 20.0° C., e.g., a portion of each forceps arm 100 may be coated with a material having an electrical conductivity of $1.0 \times 10^{-12}$ Siemens per meter at a temperature of 20.0° C. In one or more embodiments, a portion of each forceps arm 100 may be coated with a material having a thermal conductivity of less than 1.0 Watts per meter Kelvin at a temperature of 20.0° C., e.g., a portion of each forceps arm 100 may be coated with a material having a thermal conductivity of 0.25 Watts per meter Kelvin at a temperature of 20.0° C. Illustratively, a portion of each forceps arm 100 may be coated with a material having an electrical conductivity of less than $1.0 \times 10^{-8}$ Siemens per meter and a thermal conductivity of less than 1.0 Watts per meter Kelvin at a temperature of 20.0° C., e.g., a portion of each forceps arm 100 may be coated with a material having an electrical conductivity of $1.0 \times 10^{-12}$ Siemens per meter and a thermal conductivity of 0.25 Watts per meter Kelvin at a temperature of 20.0° C. In one or more embodiments, a portion of each forceps arm 100 may be coated with a material wherein a coating thickness of the material is in a range of 0.005 to 0.008 inches, e.g., a portion of each forceps arm 100 may be coated with a material wherein a coating thickness of the material is 0.0065 inches. Illustratively, a portion of each forceps arm 100 may be coated with a material wherein a coating thickness of the material is less than 0.005 inches or greater than 0.008 inches. In one or more embodiments, a portion of each forceps arm 100 may be coated with a material having an electrical conductivity of less than $1.0 \times 10^{-8}$ Siemens per meter and a thermal conductivity of less than 1.0 Watts per meter Kelvin at a temperature of 20.0° C. wherein a coating thickness of the material is in a range of 0.005 to 0.008 inches, e.g., a portion of each forceps arm 100 may be coated with a material having an electrical conductivity of $1.0 \times 10^{-12}$ Siemens per meter and a thermal conductivity of 0.25 Watts per meter Kelvin at a temperature of 20.0° C. wherein a coating thickness of the material is 0.0065 inches. Illustratively, a portion of each forceps arm 100 may be coated with a material having a material mass in a range of 0.0015 to 0.0025 pounds, e.g., a portion of each forceps arm 100 may be coated with a material having a material mass of 0.0021 pounds. In one or more embodiments, a portion of each forceps arm 100 may be coated with a material having a material mass less than 0.0015 pounds or greater than 0.0025 pounds.

Illustratively, input conductor isolation mechanism 210 may comprise a first forceps arm housing 215 and a second forceps arm housing 215. In one or more embodiments, input conductor isolation mechanism 210 may be configured to separate a first bipolar input conductor and a second bipolar input conductor, e.g., input conductor isolation mechanism 210 comprise a material with an electrical resistivity greater than $1 \times 10^{16}$ ohm meters. Illustratively, input conductor isolation mechanism 210 may comprise a material with an electrical resistivity less than or equal to $1 \times 10^{16}$ ohm meters. In one or more embodiments, input conductor isolation mechanism 210 may comprise an interface between bipolar cord 220 and forceps arms 100. Illustratively, a first bipolar input conductor and a second bipolar input conductor may be disposed within bipolar cord 220, e.g., bipolar cord 220 may be configured to separate the first bipolar input conductor and the second bipolar input conductor. In one or more embodiments, a first bipolar input conductor may be electrically connected to first forceps arm 100, e.g., the first bipolar input conductor may be disposed within input conductor housing 103. Illustratively, a second bipolar input conductor may be electrically connected to second forceps arm 100, e.g., the second bipolar input conductor may be disposed within input conductor housing 103. In one or more embodiments, a portion of first forceps arm 100 may be disposed within first forceps arm housing 215, e.g., first forceps arm proximal end 102 may be disposed within first forceps arm housing 215. Illustratively, first forceps arm 100 may be fixed within first forceps arm housing 215, e.g., by an adhesive or any suitable fixation means. In one or more embodiments, a first bipolar input conductor may be disposed within first forceps arm housing 215, e.g., the first bipolar input conductor may be electrically connected to first forceps arm 100. Illustratively, a first bipolar input conductor may be fixed within first forceps arm housing 215 wherein the first bipolar input conductor is electrically connected to first forceps arm 100. In one or more embodiments, a portion of second forceps arm 100 may be disposed within second forceps arm housing 215, e.g., second forceps arm proximal end 102 may be disposed within second forceps arm housing 215. Illustratively, second forceps arm 100 may be fixed within second forceps arm housing 215, e.g., by an adhesive or any suitable fixation means. In one or more embodiments, a second bipolar input conductor may be disposed within second forceps arm housing 215, e.g., the second bipolar input conductor may be electrically connected to second forceps arm 100. Illustratively, a second bipolar input conductor may be fixed within second forceps arm housing 215 wherein the second bipolar input conductor is electrically connected to second forceps arm 100.

In one or more embodiments, electrosurgical generator adaptor 240 may comprise a first electrosurgical generator interface 245 and a second electrosurgical generator interface 245. Illustratively, first electrosurgical generator interface 245 and second electrosurgical generator interface 245 may be configured to connect to an electrosurgical generator. In one or more embodiments, connecting first electrosurgical generator interface 245 and second electrosurgical generator interface 245 to an electrosurgical generator may be configured to electrically connect a first bipolar input conductor to a first electrosurgical generator output and to electrically connect a second bipolar input conductor to a second electrosurgical generator output. Illustratively, connecting a first bipolar input conductor to a first electrosurgical generator output may be configured to electrically connect first forceps arm 100 to the first electrosurgical generator output. In one or more embodiments, connecting a second bipolar input conductor to a second electrosurgical generator output may be configured to electrically connect second forceps arm 100 to the second electrosurgical generator output.

Illustratively, forceps arms 100 may be fixed within forceps arm housings 215 wherein forceps arm proximal ends 102 are fixed within input conductor isolation mechanism 210 and forceps arm distal ends 101 are separated by a maximum conductor tip 110 separation distance. In one or more embodiments, a surgeon may decrease a distance between first forceps arm distal end 101 and second forceps arm distal end 101, e.g., by applying a force to a lateral portion of forceps arms 100. Illustratively, a surgeon may decrease a distance between first forceps arm distal end 101 and second forceps arm distal end 101, e.g., until first forceps arm distal end 101 contacts second forceps arm distal end 101. In one or more embodiments, a contact between first forceps arm distal end 101 and second forceps arm distal end 101 may be configured to electrically connect conductor tips 110. Illustratively, an electrical connection of conductor tips 110 may be configured to close an electrical circuit. In one or more embodiments, a surgeon may increase a distance between first forceps arm distal end 101 and second forceps arm distal end 101, e.g., by reducing a force applied to a lateral portion of forceps arms 100. Illustratively, increasing a distance between first forceps arm distal end 101 and second forceps arm distal end 101 may be configured to separate conductor tips 110. In one or more embodiments, a separation of conductor tips 110 may be configured to open an electrical circuit.

Figure 3A:
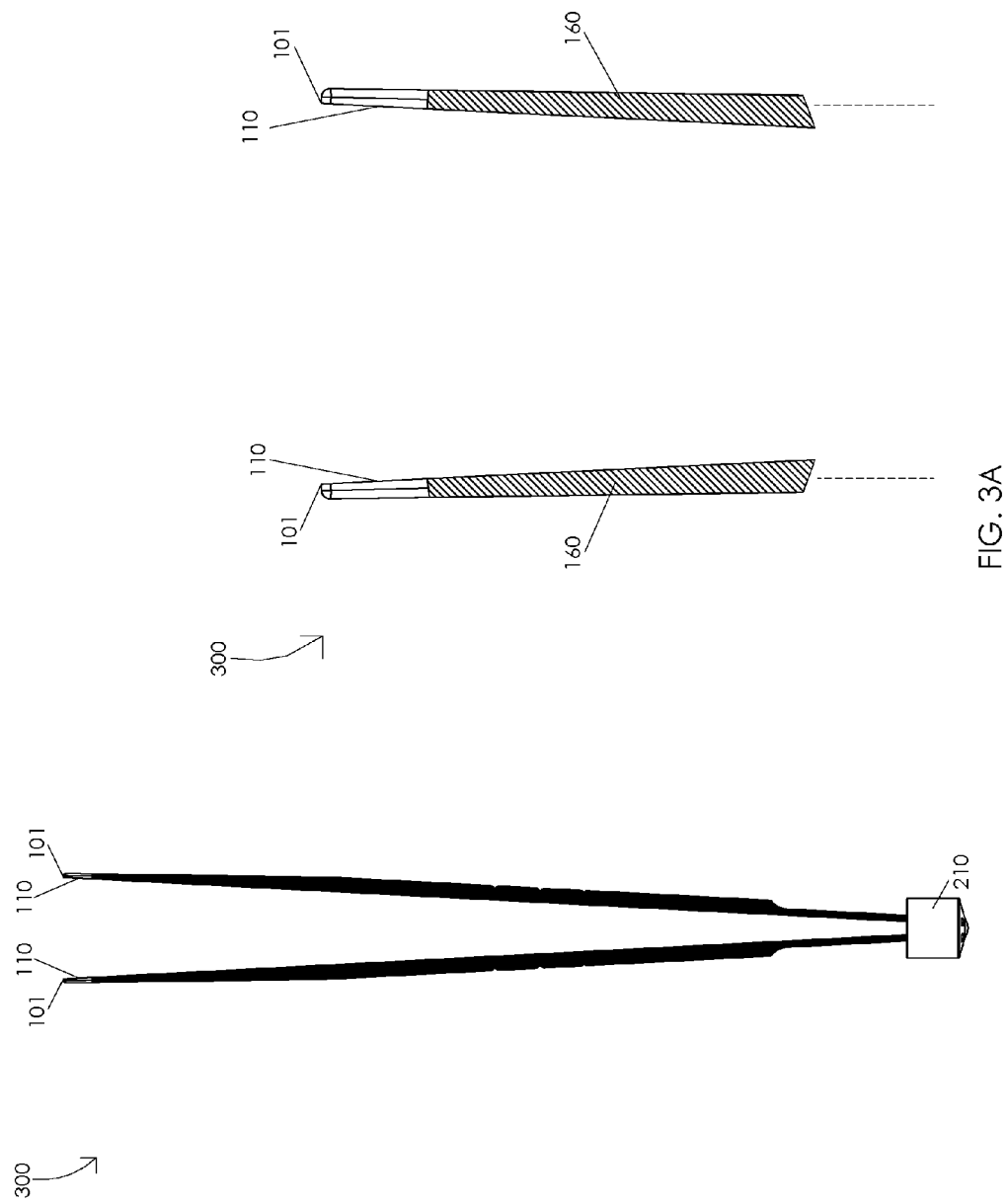
FIGS. 3A, 3B, 3C, 3D, and 3E are schematic diagrams illustrating a gradual closing of a bipolar forceps.

FIGS. 3A, 3B, 3C, 3D, and 3E are schematic diagrams illustrating a gradual closing of a bipolar forceps. FIG. 3A illustrates forceps jaws in an open orientation 300. Illustratively, forceps jaws 160 may comprise forceps jaws in an open orientation 300, e.g., when forceps arm distal ends 101 are separated by a maximum conductor tip 110 separation distance. In one or more embodiments, forceps arm distal ends 101 may be separated by a distance in a range of 0.5 to 0.7 inches when forceps jaws 160 comprise forceps jaws in an open orientation 300, e.g., forceps arm distal ends 101 may be separated by a distance of 0.625 inches when forceps jaws 160 comprise forceps jaws in an open orientation 300. Illustratively, forceps arm distal ends 101 may be separated by a distance less than 0.5 inches or greater than 0.7 inches when forceps jaws 160 comprise forceps jaws in an open orientation 300. In one or more embodiments, forceps jaws 160 may comprise forceps jaws in an open orientation 300, e.g., when no force is applied to a lateral portion of forceps arms 100.

Figure 3B:
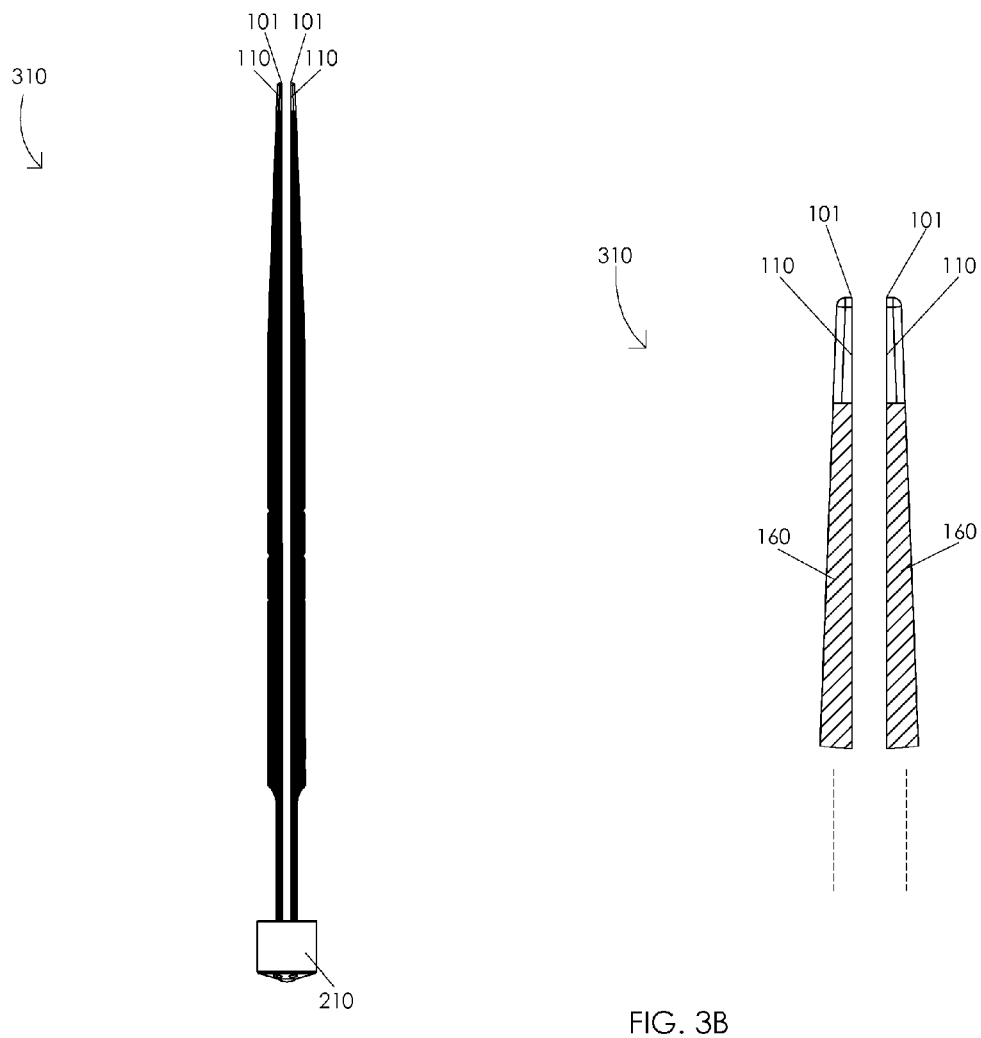

FIG. 3B illustrates forceps jaws in a partially closed orientation 310. Illustratively, an application of a force to a lateral portion of forceps arms 100 may be configured to gradually close forceps jaws 160 from forceps jaws in an open orientation 300 to forceps jaws in a partially closed orientation 310. In one or more embodiments, an application of a force to a lateral portion of forceps arms 100 may be configured to decrease a distance between first forceps arm distal end 101 and second forceps arm distal end 101. Illustratively, an application of a force having a magnitude in a range of 0.05 to 0.3 pounds to a lateral portion of forceps arms 100 may be configured to decrease a distance between first forceps arm distal end 101 and second forceps arm distal end 101, e.g., an application of a force having a magnitude of 0.2 pounds to a lateral portion of forceps arms 100 may be configured to decrease a distance between first forceps arm distal end 101 and second forceps arm distal end 101. In one or more embodiments, an application of a force having a magnitude less than 0.05 pounds or greater than 0.3 pounds to a lateral portion of forceps arms 100 may be configured to decrease a distance between first forceps arm distal end 101 and second forceps arm distal end 101. Illustratively, a decrease of a distance between first forceps arm distal end 101 and second forceps arm distal end 101 may be configured to decrease a distance between conductor tips 110. In one or more embodiments, an application of a force having a magnitude in a range of 0.05 to 0.3 pounds to a lateral portion of forceps arms 100 may be configured to gradually close forceps jaws 160 from forceps jaws in an open orientation 300 to forceps jaws in a partially closed orientation 310. Illustratively, an application of a force having a magnitude less than 0.05 pounds or greater than 0.3 pounds to a lateral portion of forceps arms 100 may be configured to gradually close forceps jaws 160 from forceps jaws in an open orientation 300 to forceps jaws in a partially closed orientation 310. In one or more embodiments, an amount of force applied to a lateral portion of forceps arms 100 configured to close forceps jaws 160 to forceps jaws in a partially closed orientation 310 and a total mass of a bipolar forceps may have a force applied to total mass ratio in a range of 1.36 to 8.19, e.g., an amount of force applied to a lateral portion of forceps arms 100 configured to close forceps jaws 160 to forceps jaws in a partially closed orientation 310 and a total mass of a bipolar forceps may have a force applied to total mass ratio of 5.46. Illustratively, an amount of force applied to a lateral portion of forceps arms 100 configured to close forceps jaws 160 to forceps jaws in a partially closed orientation 310 and a total mass of a bipolar forceps may have a force applied to total mass ratio less than 1.36 or greater than 8.19.

In one or more embodiments, a surgeon may dispose a tissue between a first forceps arm conductor tip 110 and a second forceps arm conductor tip 110, e.g., a surgeon may dispose a tumor tissue between a first forceps arm conductor tip 110 and a second forceps arm conductor tip 110. Illustratively, disposing a tissue between a first forceps arm conductor tip 110 and a second forceps arm conductor tip 110 may be configured to electrically connect the first forceps arm conductor tip 110 and the second forceps arm conductor tip 110, e.g., the tissue may electrically connect the first forceps arm conductor tip 110 and the second forceps arm conductor tip 110. In one or more embodiments, electrically connecting a first forceps arm conductor tip 110 and a second forceps arm conductor tip 110 may be configured to apply an electrical current to a tissue. Illustratively, applying an electrical current to a tissue may be configured to coagulate the tissue, cauterize the tissue, ablate the tissue, etc. In one or more embodiments, electrically connecting a first forceps arm conductor tip 110 and a second forceps arm conductor tip 110 may be configured to seal a vessel, induce hemostasis, etc.

Figure 3C:
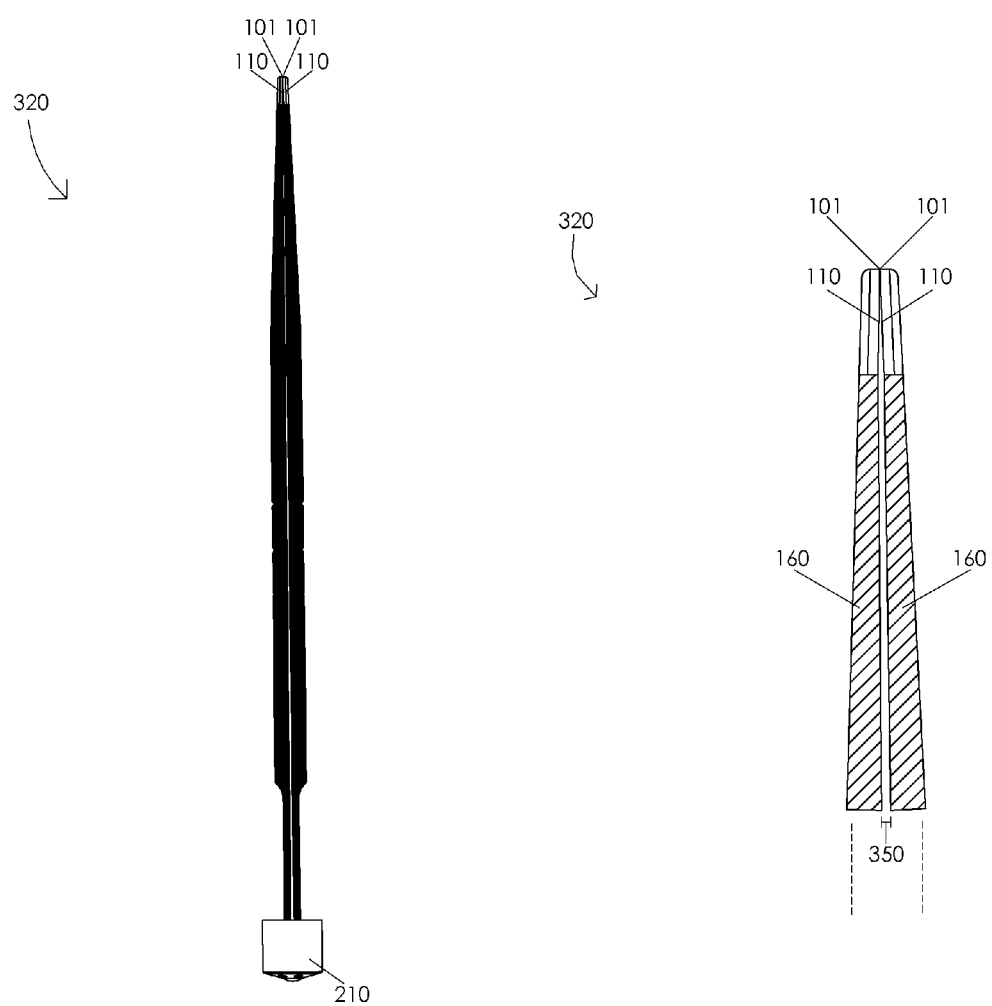

FIG. 3C illustrates forceps jaws in a first closed orientation 320. Illustratively, an application of a force to a lateral portion of forceps arms 100 may be configured to gradually close forceps jaws 160 from forceps jaws in a partially closed orientation 310 to forceps jaws in a first closed orientation 320. In one or more embodiments, an application of a force to a lateral portion of forceps arms 100 may be configured to decrease a distance between first forceps arm distal end 101 and second forceps arm distal end 101. Illustratively, a decrease of a distance between first forceps arm distal end 101 and second forceps arm distal end 101 may be configured to cause first forceps arm distal end 101 to contact second forceps arm distal end 101. In one or more embodiments, an application of a force having a magnitude in a range of 0.35 to 0.7 pounds to a lateral portion of forceps arms 100 may be configured to cause first forceps arm distal end 101 to contact second forceps arm distal end 101, e.g., an application of a force having a magnitude of 0.5 pounds to a lateral portion of forceps arms 100 may be configured to cause first forceps arm distal end 101 to contact second forceps arm distal end 101. Illustratively, an application of a force having a magnitude less than 0.35 pounds or greater than 0.7 pounds to a lateral portion of forceps arms 100 may be configured to cause first forceps arm distal end 101 to contact second forceps arm distal end 101. In one or more embodiment, an application of a force having a magnitude in a range of 0.35 to 0.7 pounds to a lateral portion of forceps arms 100 may be configured to gradually close forceps jaws 160 from forceps jaws in a partially closed orientation 310 to forceps jaws in a first closed orientation 320. Illustratively, an application of a force having a magnitude less than 0.35 pounds or greater than 0.7 pounds to a lateral portion of forceps arms 100 may be configured to gradually close forceps jaws 160 from forceps jaws in a partially closed orientation 310 to forceps jaws in a first closed orientation 320. In one or more embodiments, an amount of force applied to a lateral portion of forceps arms 100 configured to close forceps jaws 160 to forceps jaws in a first closed orientation 320 and a total mass of a bipolar forceps may have a force applied to total mass ratio in a range of 9.56 to 19.11, e.g., an amount of force applied to a lateral portion of forceps arms 100 configured to close forceps jaws 160 to forceps jaws in a first closed orientation 320 and a total mass of a bipolar forceps may have a force applied to total mass ratio of 13.65. Illustratively, an amount of force applied to a lateral portion of forceps arms 100 configured to close forceps jaws 160 to forceps jaws in a first closed orientation 320 and a total mass of a bipolar forceps may have a force applied to total mass ratio less than 9.56 or greater than 19.11.

In one or more embodiments, forceps jaws 160 may comprise forceps jaws in a first closed orientation 320, e.g., when first forceps arm distal end 101 contacts second forceps arm distal end 101 and no other portion of first forceps arm 100 contacts second forceps arm 100. Illustratively, forceps jaws 160 may comprise forceps jaws in a first closed orientation 320, e.g., when a distal end of a first forceps arm conductor tip 110 contacts a distal end of a second forceps arm conductor tip 110 and no other portion of first forceps arm 100 contacts second forceps arm 100. In one or more embodiments, first forceps arm conductor tip 110 and second forceps arm conductor tip 110 may have a contact area in a range of 0.0005 to 0.002 square inches when forceps jaws 160 comprise forceps jaws in a first closed orientation 320, e.g., first forceps arm conductor tip 110 and second forceps arm conductor tip 110 may have a contact area of 0.0016 square inches when forceps jaws 160 comprise forceps jaws in a first closed orientation 320. Illustratively, first forceps arm conductor tip 110 and second forceps arm conductor tip 110 may have a contact area of less than 0.0005 square inches or greater than 0.002 square inches when forceps jaws 160 comprise forceps jaws in a first closed orientation 320. In one or more embodiments, a proximal end of a first forceps arm conductor tip 110 may be separated from a proximal end of a second forceps arm conductor tip 110, e.g., when forceps jaws 160 comprise forceps jaws in a first closed orientation 320. Illustratively, a proximal end of a first forceps arm conductor tip 110 may be separated from a proximal end of a second forceps arm conductor tip 110 by a distance in a range of 0.005 to 0.015 inches when forceps jaws 160 comprise forceps jaws in a first closed orientation 320, e.g., a proximal end of a first forceps arm conductor tip 110 may be separated from a proximal end of a second forceps arm conductor tip 110 by a distance of 0.01 inches when forceps jaws 160 comprise forceps jaws in a first closed orientation 320. In one or more embodiments, a proximal end of a first forceps arm conductor tip 110 may be separated from a proximal end of a second forceps arm conductor tip 110 by a distance less than 0.005 inches or greater than 0.015 inches when forceps jaws 160 comprise forceps jaws in a first closed orientation 320.

Illustratively, forceps jaws 160 may comprise forceps jaws in a first closed orientation 320, e.g., when a distal end of a first forceps jaw 160 contacts a distal end of a second forceps jaw 160 and no other portion of first forceps arm 100 contacts second forceps arm 100. In one or more embodiments, a proximal end of a first forceps jaw 160 may be separated from a proximal end of a second forceps jaw 160 by a first separation distance 350, e.g., when forceps jaws 160 comprise forceps jaws in a first closed orientation 320. Illustratively, a proximal end of a first forceps jaw 160 may be separated from a proximal end of a second forceps jaw 160 by a first separation distance 350 in a range of 0.05 to 0.15 inches when forceps jaws 160 comprise forceps jaws in a first closed orientation 320, e.g., a proximal end of a first forceps jaw 160 may be separated from a proximal end of a second forceps jaw 160 by a first separation distance 350 of 0.1 inches when forceps jaws 160 comprise forceps jaws in a first closed orientation 320. In one or more embodiments, a proximal end of a first forceps jaw 160 may be separated from a proximal end of a second forceps jaw 160 by a first separation distance 350 less than 0.05 inches or greater than 0.15 inches when forceps jaws 160 comprise forceps jaws in a first closed orientation 320.

Illustratively, forceps jaws 160 may comprise forceps jaws in a first closed orientation 320, e.g., when a distal end of a first forceps arm conductor tip 110 contacts a distal end of a second forceps arm conductor tip 110. In one or more embodiments, a contact between a distal end of a first forceps arm conductor tip 110 and a distal end of a second forceps arm conductor tip 110 may be configured to electrically connect the first forceps arm conductor tip 110 and the second forceps arm conductor tip 110. Illustratively, forceps jaws 160 may comprise forceps jaws in a first closed orientation 320, e.g., when a first forceps arm conductor tip 110 is electrically connected to a second forceps arm conductor tip 110. In one or more embodiments, an electrical connection of a first forceps arm conductor tip 110 and a second forceps arm conductor tip 110 may be configured to cause an electrical current to flow from the first forceps arm conductor tip 110 into the second forceps arm conductor tip 110. Illustratively, an electrical connection of a first forceps arm conductor tip 110 and a second forceps arm conductor tip 110 may be configured to cause an electrical current to flow from the second forceps arm conductor tip 110 into the first forceps arm conductor tip 110. In one or more embodiments, electrically connecting a first forceps arm conductor tip 110 and a second forceps arm conductor tip 110 may be configured to increase a temperature of forceps arm distal ends 101, e.g., a surgeon may contact a tissue with forceps arm distal ends 101 to cauterize the tissue, coagulate the tissue, etc.

Figure 3D:
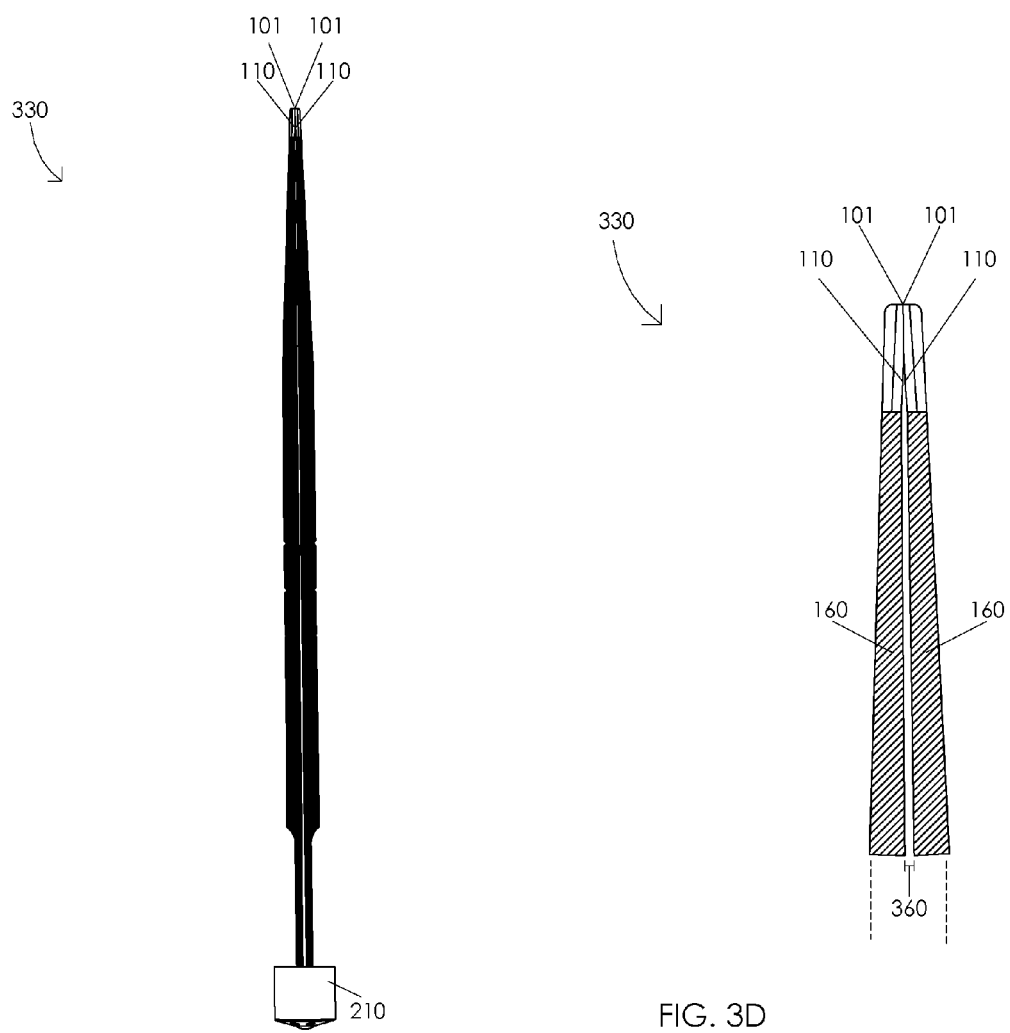

FIG. 3D illustrates forceps jaws in a second closed orientation 330. Illustratively, an application of a force to a lateral portion of forceps arms 100 may be configured to gradually close forceps jaws 160 from forceps jaws in a first closed orientation 320 to forceps jaws in a second closed orientation 330. In one or more embodiments, an application of a force to a lateral portion of forceps arms 100 may be configured to decrease a distance between a proximal end of first forceps arm conductor tip 110 and a proximal end of second forceps arm conductor tip 110. Illustratively, an application of a force to a lateral portion of forceps arms 100 may be configured to flex forceps jaws in a first closed orientation 320, e.g., an application of a force to a lateral portion of forceps arms 100 may be configured to gradually increase a contact area between first forceps arm conductor tip 110 and second forceps arm conductor tip 110. In one or more embodiments, an application of a force having a magnitude in a range of 0.8 to 1.4 pounds to a lateral portion of forceps arms 100 may be configured to gradually increase a contact area between first forceps arm conductor tip 110 and second forceps arm conductor tip 110, e.g., an application of a force having a magnitude of 1.1 pounds to a lateral portion of forceps arms 100 may be configured to gradually increase a contact area between first forceps arm conductor tip 110 and second forceps arm conductor tip 110. Illustratively, an application of a force having a magnitude less than 0.8 pounds or greater than 1.4 pounds to a lateral portion of forceps arms 100 may be configured to gradually increase a contact area between first forceps arm conductor tip 110 and second forceps arm conductor tip 110. In one or more embodiments, an application of a force having a magnitude in a range of 0.8 to 1.4 pounds to a lateral portion of forceps arms 100 may be configured to gradually close forceps jaws 160 from forceps jaws in a first closed orientation 320 to forceps jaws in a second closed orientation 330. Illustratively, an application of a force having a magnitude less than 0.8 pounds or greater than 1.4 pounds to a lateral portion of forceps arms 100 may be configured to gradually close forceps jaws 160 from forceps jaws in a first closed orientation 320 to forceps jaws in a second closed orientation 330. In one or more embodiments, an amount of force applied to a lateral portion of forceps arms 100 configured to close forceps jaws 160 to forceps jaws in a second closed orientation 330 and a total mass of a bipolar forceps may have a force applied to total mass ratio in a range of 21.84 to 38.22, e.g., an amount of force applied to a lateral portion of forceps arms 100 configured to close forceps jaws 160 to forceps jaws in a second closed orientation 330 and a total mass of a bipolar forceps may have a force applied to total mass ratio of 30.03. Illustratively, an amount of force applied to a lateral portion of forceps arms 100 configured to close forceps jaws 160 to forceps jaws in a second closed orientation 330 and a total mass of a bipolar forceps may have a force applied to total mass ratio less than 21.84 or greater than 38.22.

In one or more embodiments, first forceps arm conductor tip 110 and second forceps arm conductor tip 110 may have a contact area in a range of 0.001 to 0.005 square inches when forceps jaws 160 comprise forceps jaws in a second closed orientation 330, e.g., first forceps arm conductor tip 110 and second forceps arm conductor tip 110 may have a contact area of 0.0025 square inches when forceps jaws 160 comprise forceps jaws in a second closed orientation 330. Illustratively, first forceps arm conductor tip 110 and second forceps arm conductor tip 110 may have a contact area less than 0.001 square inches or greater than 0.005 square inches when forceps jaws 160 comprise forceps jaws in a second closed orientation 330. In one or more embodiments, a proximal end of a first forceps arm conductor tip 110 may be separated from a proximal end of a second forceps arm conductor tip 110, e.g., when forceps jaws 160 comprise forceps jaws in a second closed orientation 330. Illustratively, a proximal end of a first forceps arm conductor tip 110 may be separated from a proximal end of a second forceps arm conductor tip 110 by a distance in a range of 0.001 to 0.0049 inches when forceps jaws 160 comprise forceps jaws in a second closed orientation 330, e.g., a proximal end of a first forceps arm conductor tip 110 may be separated from a proximal end of a second forceps arm conductor tip 110 by a distance of 0.0025 inches when forceps jaws 160 comprise forceps jaws in a second closed orientation 330. In one or more embodiments, a proximal end of a first forceps arm conductor tip 110 may be separated from a proximal end of a second forceps arm conductor tip 110 by a distance less than 0.001 inches or greater than 0.0049 inches when forceps jaws 160 comprise forceps jaws in a second closed orientation 330.

Illustratively, forceps jaws 160 may comprise forceps jaws in a second closed orientation 330, e.g., when a distal end of a first forceps jaw 160 contacts a distal end of a second forceps jaw 160. In one or more embodiments, a proximal end of a first forceps jaw 160 may be separated from a proximal end of a second forceps jaw 160 by a second separation distance 360, e.g., when forceps jaws 160 comprise forceps jaws in a second closed orientation 330. Illustratively, a proximal end of a first forceps jaw 160 may be separated from a proximal end of a second forceps jaw 160 by a second separation distance 360 in a range of 0.01 to 0.049 inches when forceps jaws 160 comprise forceps jaws in a second closed orientation 330, e.g., a proximal end of a first forceps jaw 160 may be separated from a proximal end of a second forceps jaw 160 by a second separation distance 360 of 0.03 inches when forceps jaws 160 comprise forceps jaws in a second closed orientation 330. In one or more embodiments, a proximal end of a first forceps jaw 160 may be separated from a proximal end of a second forceps jaw 160 by a second separation distance 360 less than 0.01 inches or greater than 0.049 inches when forceps jaws 160 comprise forceps jaws in a second closed orientation 330.

Illustratively, forceps jaws 160 may comprise forceps jaws in a second closed orientation 330, e.g., when a first forceps arm conductor tip 110 contacts a second forceps arm conductor tip 110. In one or more embodiments, a contact between a first forceps arm conductor tip 110 and a second forceps arm conductor tip 110 may be configured to electrically connect the first forceps arm conductor tip 110 and the second forceps arm conductor tip 110. Illustratively, forceps jaws 160 may comprise forceps jaws in a second closed orientation 330, e.g., when a first forceps arm conductor tip 110 is electrically connected to a second forceps arm conductor tip 110. In one or more embodiments, an electrical connection of a first forceps arm conductor tip 110 and a second forceps arm conductor tip 110 may be configured to cause an electrical current to flow from the first forceps arm conductor tip 110 into the second forceps arm conductor tip 110. Illustratively, an electrical connection of a first forceps arm conductor tip 110 and a second forceps arm conductor tip 110 may be configured to cause an electrical current to flow from the second forceps arm conductor tip 110 into the first forceps arm conductor tip 110. In one or more embodiments, electrically connecting a first forceps arm conductor tip 110 and a second forceps arm conductor tip 110 may be configured to increase a temperature of forceps arm conductor tips 110, e.g., a surgeon may contact a tissue with forceps arm conductor tips 110 to cauterize the tissue, coagulate the tissue, etc.

Figure 3E:
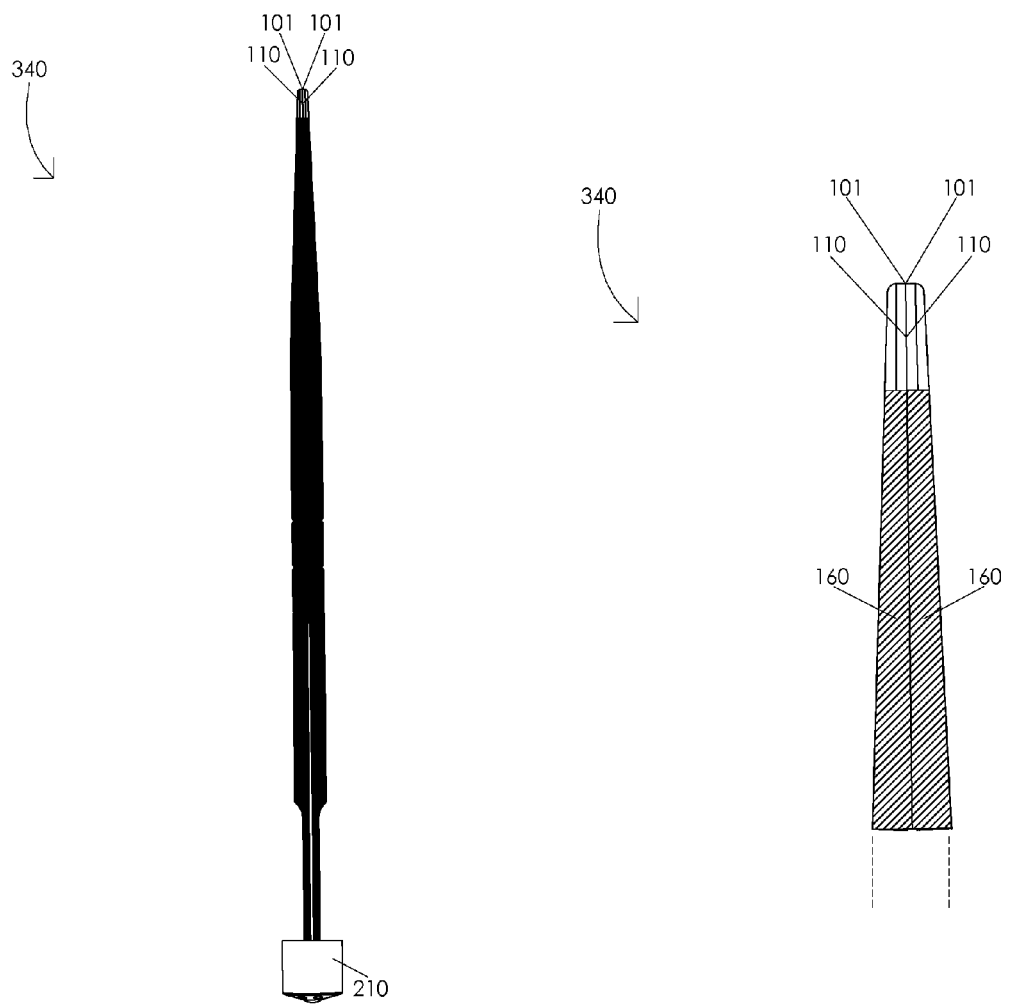

FIG. 3E illustrates forceps jaws in a fully closed orientation 340. Illustratively, an application of a force to a lateral portion of forceps arms 100 may be configured to gradually close forceps jaws 160 from forceps jaws in a second closed orientation 330 to forceps jaws in a fully closed orientation 340. In one or more embodiments, an application of a force to a lateral portion of forceps arms 100 may be configured to decrease a distance between a proximal end of first forceps arm conductor tip 110 and a proximal end of second forceps arm conductor tip 110. Illustratively, an application of a force to a lateral portion of forceps arms 100 may be configured to gradually increase a contact area between first forceps arm conductor tip 110 and second forceps arm conductor tip 110 until a proximal end of first forceps arm conductor tip 110 contacts a proximal end of second forceps arm conductor tip 110. In one or more embodiments, a proximal end of first forceps arm conductor tip 110 may contact a proximal end of second forceps arm conductor tip 110, e.g., when forceps jaws 160 comprise forceps jaws in a fully closed orientation 340. Illustratively, first forceps arm conductor tip 110 and second forceps arm conductor tip 110 may have a maximum contact area, e.g., when forceps jaws 160 comprise forceps jaws in a fully closed orientation 340. In one or more embodiments, first forceps arm conductor tip 110 and second forceps arm conductor tip 110 may have a contact area in a range of 0.01 to 0.015 square inches when forceps jaws 160 comprise forceps jaws in a fully closed orientation 340, e.g., first forceps arm conductor tip 110 and second forceps arm conductor tip 110 may have a contact area of 0.0125 square inches when forceps jaws 160 comprise forceps jaws in a fully closed orientation 340. Illustratively, first forceps arm conductor tip 110 and second forceps arm conductor tip 110 may have a contact area less than 0.01 square inches or greater than 0.015 square inches when forceps jaws 160 comprise forceps jaws in a fully closed orientation 340.

In one or more embodiments, an application of a force to a lateral portion of forceps arms 100 may be configured to gradually increase a contact area between first forceps jaw 160 and second forceps jaw 160. Illustratively, an application of a force to a lateral portion of forceps arms 100 may be configured to gradually increase a contract area between first forceps jaw 160 and second forceps jaw 160. In one or more embodiments, an application of a force to a lateral portion of forceps arms 100 may be configured to gradually increase a contact area between first forceps jaw 160 and second forceps jaw 160 until a proximal end of first forceps jaw 160 contacts a proximal end of second forceps jaw 160. Illustratively, a proximal end of first forceps jaw 160 may contact a proximal end of second forceps jaw 160, e.g., when forceps jaws 160 comprise forceps jaws in a fully closed orientation 340. In one or more embodiments, first forceps jaw 160 and second forceps jaw 160 may have a maximum contact area, e.g., when forceps jaws 160 comprise forceps jaws in a fully closed orientation 340. Illustratively, an application of a force having a magnitude in a range of 1.5 to 3.3 pounds to a lateral portion of forceps arms 100 may be configured to gradually close forceps jaws 160 from forceps jaws in a second closed orientation 330 to forceps jaws in a fully closed orientation 340, e.g., an application of a force having a magnitude of 2.5 pounds to a lateral portion of forceps arms may be configured to gradually close forceps jaws 160 from forceps jaws in a second closed orientation 330 to forceps jaws in a fully closed orientation 340. In one or more embodiments, an application of a force having a magnitude less than 1.5 pounds or greater than 3.3 pounds to a lateral portion of forceps arms 100 may be configured to gradually close forceps jaws 160 from forceps jaws in a second closed orientation 330 to forceps jaws in a fully closed orientation 340. Illustratively, an amount of force applied to a lateral portion of forceps arms 100 configured to close forceps jaws 160 to forceps jaws in a fully closed orientation 340 and a total mass of a bipolar forceps may have a force applied to total mass ratio in a range of 40.95 to 90.10, e.g., an amount of force applied to a lateral portion of forceps arms 100 configured to close forceps jaws 160 to forceps jaws in a fully closed orientation 340 and a total mass of a bipolar forceps may have a force applied to total mass ratio of 68.26. In one or more embodiments, an amount of force applied to a lateral portion of forceps arms 100 configured to close forceps jaws 160 to forceps jaws in a fully closed orientation 340 and a total mass of a bipolar forceps may have a force applied to total mass ratio less than 40.95 or greater than 90.10.

Figure 4A:
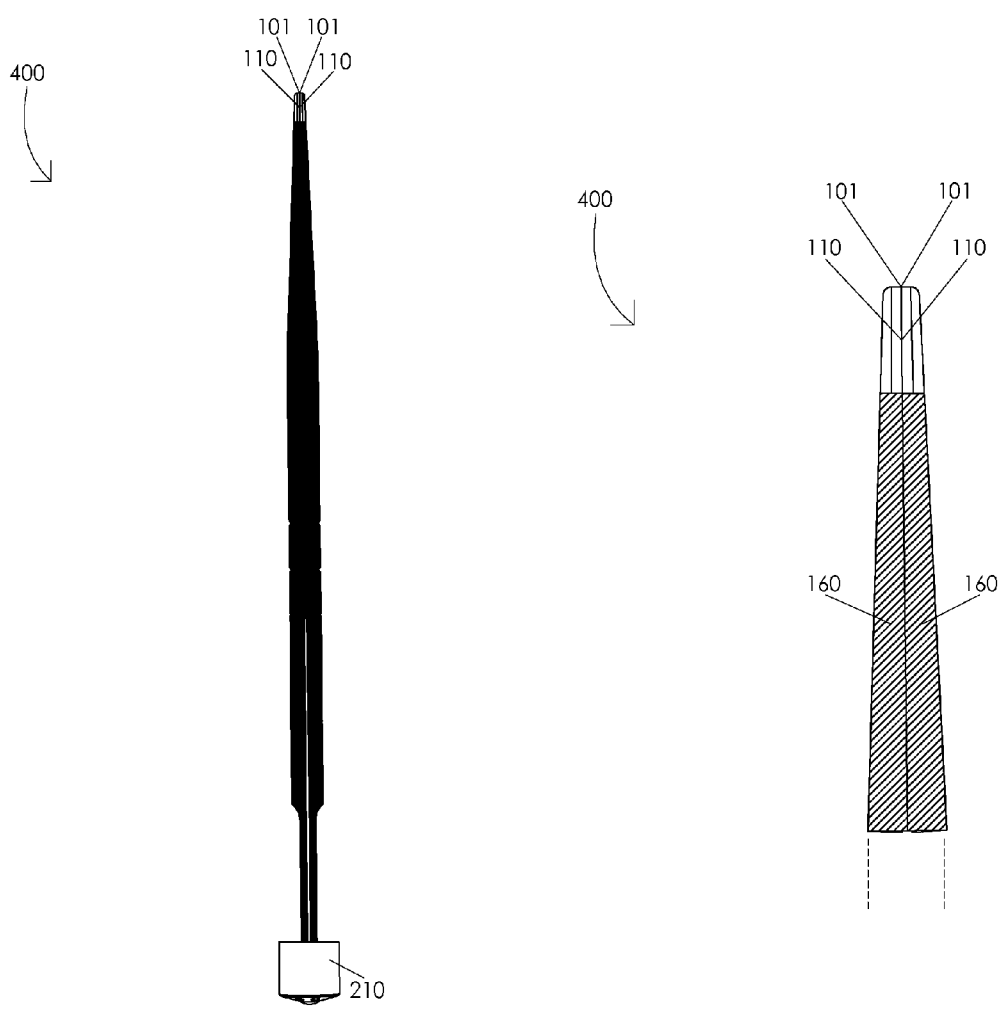
FIGS. 4A, 4B, 4C, 4D, and 4E are schematic diagrams illustrating a gradual opening of a bipolar forceps.

FIGS. 4A, 4B, 4C, 4D, and 4E are schematic diagrams illustrating a gradual opening of a bipolar forceps. FIG. 4A illustrates forceps jaws in a closed orientation 400. Illustratively, forceps jaws 160 may comprise forceps jaws in a closed orientation 400, e.g., when a first forceps arm conductor tip 110 contacts a second forceps arm conductor tip 110. In one or more embodiments, forceps jaws 160 may comprise forceps jaws in a closed orientation 400, e.g., when a distal end of a first forceps arm conductor tip 110 contacts a distal end of a second forceps arm conductor tip 110 and a proximal end of the first forceps arm conductor tip 110 contacts a proximal end of the second forceps arm conductor tip 110. Illustratively, forceps jaws 160 may comprise forceps jaws in a closed orientation 400, e.g., when a first forceps jaw 160 contacts a second forceps jaw 160. In one or more embodiments, forceps jaws 160 may comprise forceps jaws in a closed orientation 400, e.g., when a distal end of a first forceps jaw 160 contacts a distal end of a second forceps jaw 160 and a proximal end of the first forceps jaw 160 contacts a proximal end of the second forceps jaw 160. Illustratively, forceps jaws 160 may comprise forceps jaws in a closed orientation 400 when a force having a magnitude greater than 1.5 pounds is applied to a lateral portion of forceps arms 100, e.g., forceps jaws 160 may comprise forceps jaws in a closed orientation 400 when a force having a magnitude of 2.5 pounds is applied to a lateral portion of forceps arms 100. In one or more embodiments, forceps jaws 160 may comprise forceps jaws in a closed orientation 400 when a force less than or equal to 1.5 pounds is applied to a lateral portion of forceps arms 100.

Figure 4B:
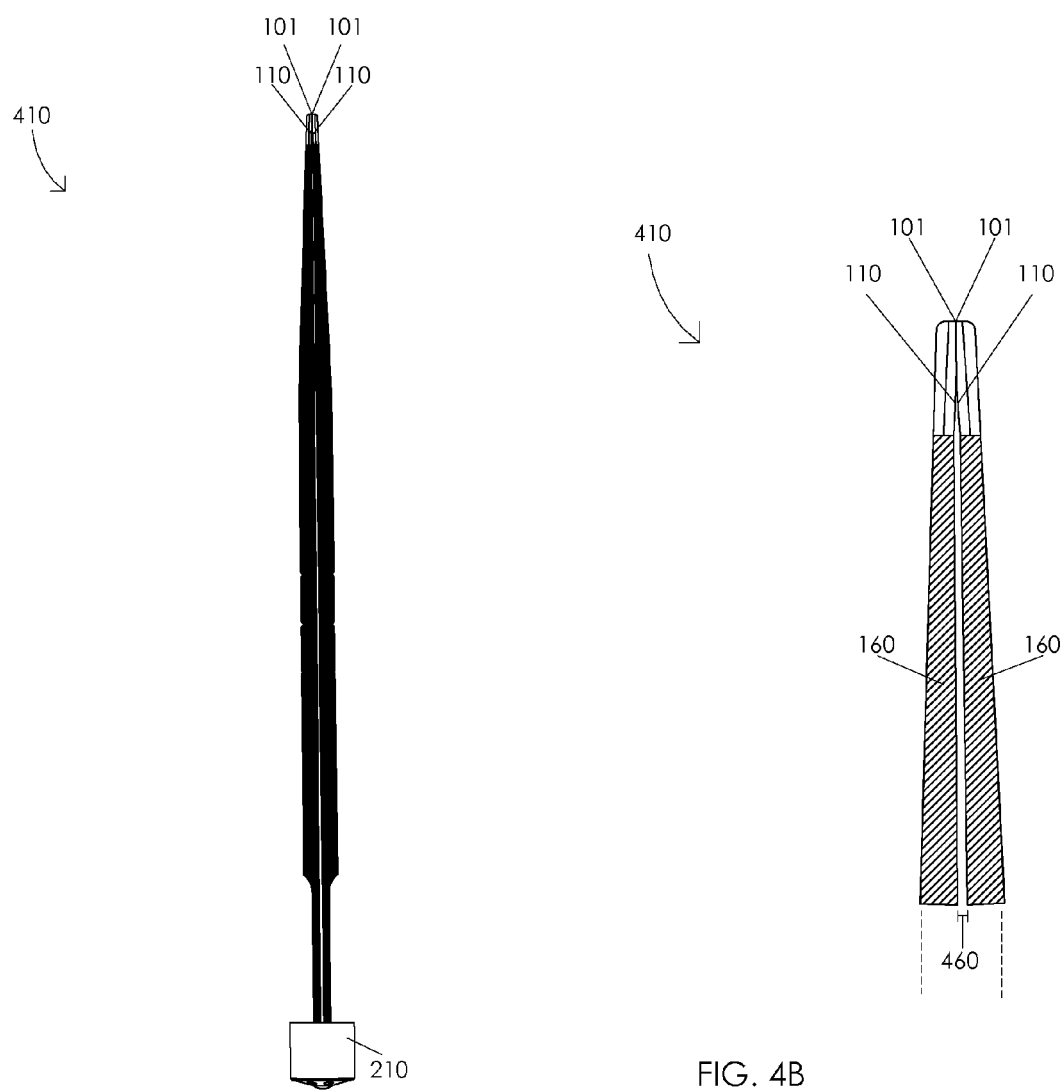

FIG. 4B illustrates forceps jaws in a first partially closed orientation 410. Illustratively, a reduction of a force applied to a lateral portion of forceps arms 100 may be configured to gradually open forceps jaws 160 from forceps jaws in a closed orientation 400 to forceps jaws in a first partially closed orientation 410. In one or more embodiments, a reduction of a force applied to a lateral portion of forceps arms 100 may be configured to separate proximal ends of forceps jaws 160. Illustratively, a reduction of a force applied to a lateral portion of forceps arms 100 may be configured to increase a distance between a proximal end of first forceps jaw 160 and a proximal end of second forceps jaw 160. In one or more embodiments, a proximal end of a first forceps jaw 160 may be separated from a proximal end of a second forceps jaw 160 by a first partially closed separation distance 460, e.g., when forceps jaws 160 comprise forceps jaws in a first partially closed orientation 410. Illustratively, a proximal end of a first forceps jaw 160 may be separated from a proximal end of a second forceps jaw 160 by a first partially closed separation distance 460 in a range of 0.01 to 0.049 inches when forceps jaws 160 comprise forceps jaws in a first partially closed orientation 410, e.g., a proximal end of a first forceps jaw 160 may be separated from a proximal end of a second forceps jaw 160 by a first partially closed separation distance 460 of 0.03 inches when forceps jaws 160 comprise forceps jaws in a first partially closed orientation 410. In one or more embodiments, a proximal end of a first forceps jaw 160 may be separated from a proximal end of a second forceps jaw 160 by a first partially closed separation distance 460 less than 0.01 inches or greater than 0.049 inches when forceps jaws 160 comprise forceps jaws in a first partially closed orientation 410. Illustratively, a reduction of a force applied to a lateral portion of forceps arms 100 may be configured to separate proximal ends of forceps arm conductor tips 110. In one or more embodiments, a reduction of a force applied to a lateral portion of forceps arms 100 may be configured to increase a separation distance between a proximal end of first forceps arm conductor tip 110 and a proximal end of second forceps arm conductor tip 110. Illustratively, a reduction of a force applied to a lateral portion of forceps arms 100 may be configured to reduce a contact area between first forceps arm conductor tip 110 and second forceps arm conductor tip 110. In one or more embodiments, a reduction of a force applied to a lateral portion of forceps arms 100 may be configured to spread a tissue, dissect a tissue, etc. Illustratively, a surgeon may insert forceps arm distal ends 101 into a tissue, e.g., when forceps jaws 160 comprise forceps jaws in a closed orientation 400. In one or more embodiments, the surgeon may reduce a force applied to a lateral portion of forceps arms 100 and gradually open forceps jaws 160 from forceps jaws in a closed orientation 400 to forceps jaws in a first partially closed orientation 410. Illustratively, gradually opening forceps jaws 160 from forceps jaws in a closed orientation 400 to forceps jaws in a first partially closed orientation 410 may be configured to spread the tissue, dissect the tissue, etc.

Figure 4C:
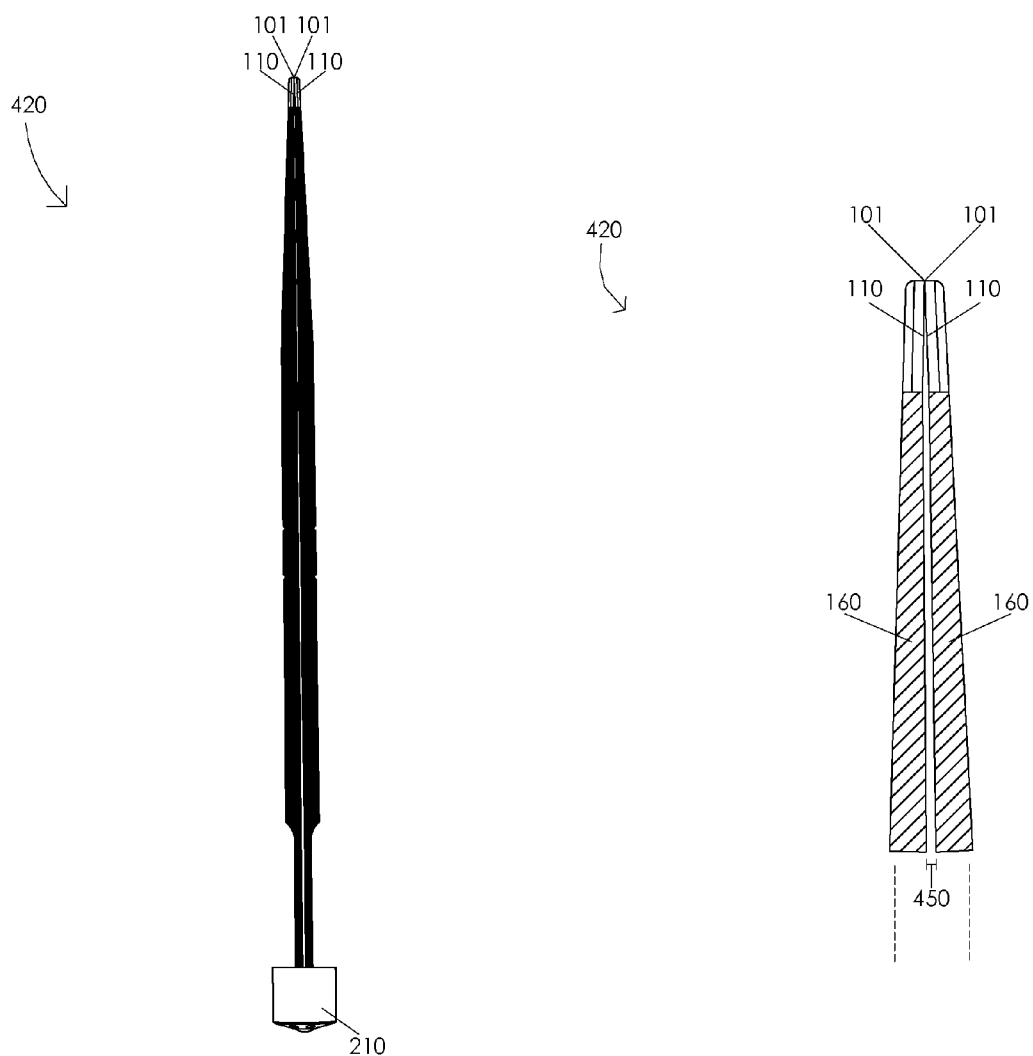

FIG. 4C illustrates forceps jaws in a second partially closed orientation 420. Illustratively, a reduction of a force applied to a lateral portion of forceps arms 100 may be configured to gradually open forceps jaws 160 from forceps jaws in a first partially closed orientation 410 to forceps jaws in a second partially closed orientation 420. In one or more embodiments, a reduction of a force applied to a lateral portion of forceps arms 100 may be configured to separate proximal ends of forceps jaws 160. Illustratively, a reduction of a force applied to a lateral portion of forceps arms 100 may be configured to increase a distance between a proximal end of first forceps jaw 160 and a proximal end of second forceps jaw 160. In one or more embodiments, a proximal end of a first forceps jaw 160 may be separated from a proximal end of a second forceps jaw 160 by a second partially closed separation distance 450, e.g., when forceps jaws 160 comprise forceps jaws in a second partially closed orientation 420. Illustratively, a proximal end of a first forceps jaw 160 may be separated from a proximal end of a second forceps jaw 160 by a second partially closed separation distance 450 in a range of 0.05 to 0.15 inches when forceps jaws 160 comprise forceps jaws in a second partially closed orientation 420, e.g., a proximal end of a first forceps jaw 160 may be separated from a proximal end of a second forceps jaw 160 by a second partially closed separation distance 450 of 0.1 inches when forceps jaws 160 comprise forceps jaws in a second partially closed orientation 420. In one or more embodiments, a proximal end of a first forceps jaw 160 may be separated from a proximal end of a second forceps jaw 160 by a second partially closed separation distance 450 less than 0.05 inches or greater than 0.15 inches when forceps jaws 160 comprise forceps jaws in a second partially closed orientation 420. Illustratively, a reduction of a force applied to a lateral portion of forceps arms 100 may be configured to separate proximal ends of forceps arm conductor tips 110. In one or more embodiments, a reduction of a force applied to a lateral portion of forceps arms 100 may be configured to increase a separation distance between a proximal end of first forceps arm conductor tip 110 and a proximal end of second forceps arm conductor tip 110. Illustratively, a reduction of a force applied to a lateral portion of forceps arms 100 may be configured to reduce a contact area between first forceps arm conductor tip 110 and second forceps arm conductor tip 110. In one or more embodiments, a reduction of a force applied to a lateral portion of forceps arms 100 may be configured to spread a tissue, dissect a tissue, etc. Illustratively, a surgeon may insert forceps arm distal ends 101 into a tissue, e.g., when forceps jaws 160 comprise forceps jaws in a first partially closed orientation 410. In one or more embodiments, the surgeon may reduce a force applied to a lateral portion of forceps arms 100 and gradually open forceps jaws 160 from forceps jaws in a first partially closed orientation 410 to forceps jaws in a second partially closed orientation 420. Illustratively, gradually opening forceps jaws 160 from forceps jaws in a first partially closed orientation 410 to forceps jaws in a second partially closed orientation 420 may be configured to spread the tissue, dissect the tissue, etc.

Figure 4D:
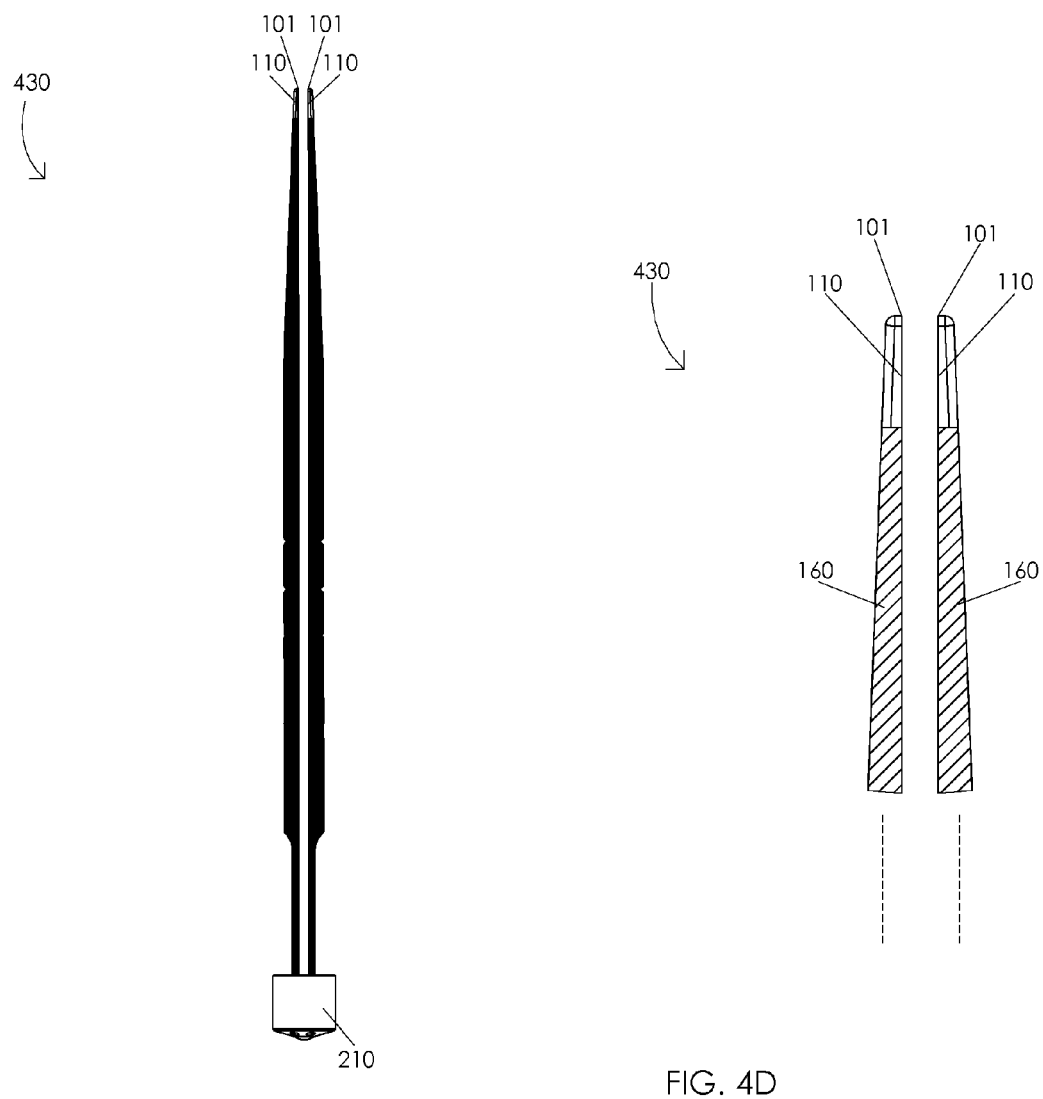

FIG. 4D illustrates forceps jaws in a partially open orientation 430. Illustratively, a reduction of a force applied to a lateral portion of forceps arms 100 may be configured to gradually open forceps jaws 160 from forceps jaws in a second partially closed orientation 420 to forceps jaws in a partially open orientation 430. In one or more embodiments, a distal end of first forceps jaw 160 may be separated from a distal end of second forceps jaw 160, e.g., when forceps jaws 160 comprise forceps jaws in a partially open orientation 430. Illustratively, a distal end of first forceps arm conductor tip 110 may be separated from a distal end of second forceps arm conductor tip 110, e.g., when forceps jaws 160 comprise forceps jaws in a partially open orientation 430. In one or more embodiments, a reduction of a force applied to a lateral portion of forceps arms 100 may be configured to electrically disconnect first forceps arm conductor tip 110 and second forceps arm conductor tip 110. Illustratively, first forceps arm conductor tip 110 may be electrically disconnected from second forceps arm conductor tip 110, e.g., when forceps jaws 160 comprise forceps jaws in a partially open orientation 430. In one or more embodiments, a reduction of a force applied to a lateral portion of forceps arms 100 may be configured to spread a tissue, dissect a tissue, etc. Illustratively, a surgeon may insert forceps arm distal ends 101 into a tissue, e.g., when forceps jaws 160 comprise forceps jaws in a second partially closed orientation 420. In one or more embodiments, the surgeon may reduce a force applied to a lateral portion of forceps arms 100 and gradually open forceps jaws 160 from forceps jaws in a second partially closed orientation 420 to forceps jaws in a partially open orientation 430. Illustratively, gradually opening forceps jaws 160 from forceps jaws in a second partially closed orientation 420 to forceps jaws in a partially open orientation 430 may be configured to spread the tissue, dissect the tissue, etc.

Figure 4E:
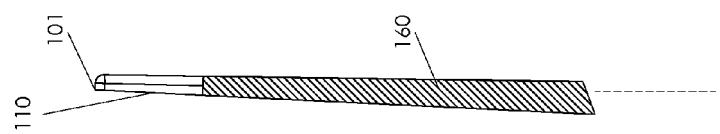
Figure 4E:
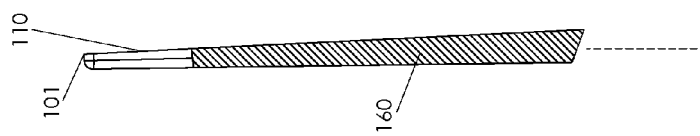
Figure 4E:
Figure 4E:
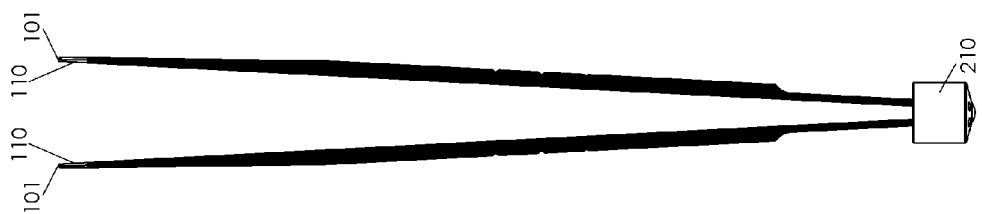
Figure 4E:

FIG. 4E illustrates forceps jaws in a fully open orientation 440. Illustratively, a reduction of a force applied to a lateral portion of forceps arms 100 may be configured to gradually open forceps jaws 160 from forceps jaws in a partially open orientation 430 to forceps jaws in a fully open orientation 440. In one or more embodiments, forceps arm distal ends 101 may be separated by a distance in a range of 0.5 to 0.7 inches when forceps jaws 160 comprise forceps jaws in a fully open orientation 440, e.g., forceps arm distal ends 101 may be separated by a distance of 0.625 inches when forceps jaws 160 comprise forceps jaws in a fully open orientation 440. Illustratively, forceps arm distal ends 101 may be separated by a distance less than 0.5 inches or greater than 0.7 inches when forceps jaws 160 comprise forceps jaws in a fully open orientation 440. In one or more embodiments, forceps jaws 160 may comprise forceps jaws in a fully open orientation 440, e.g., when no force is applied to a lateral portion of forceps arms 100.

Figure 5B:
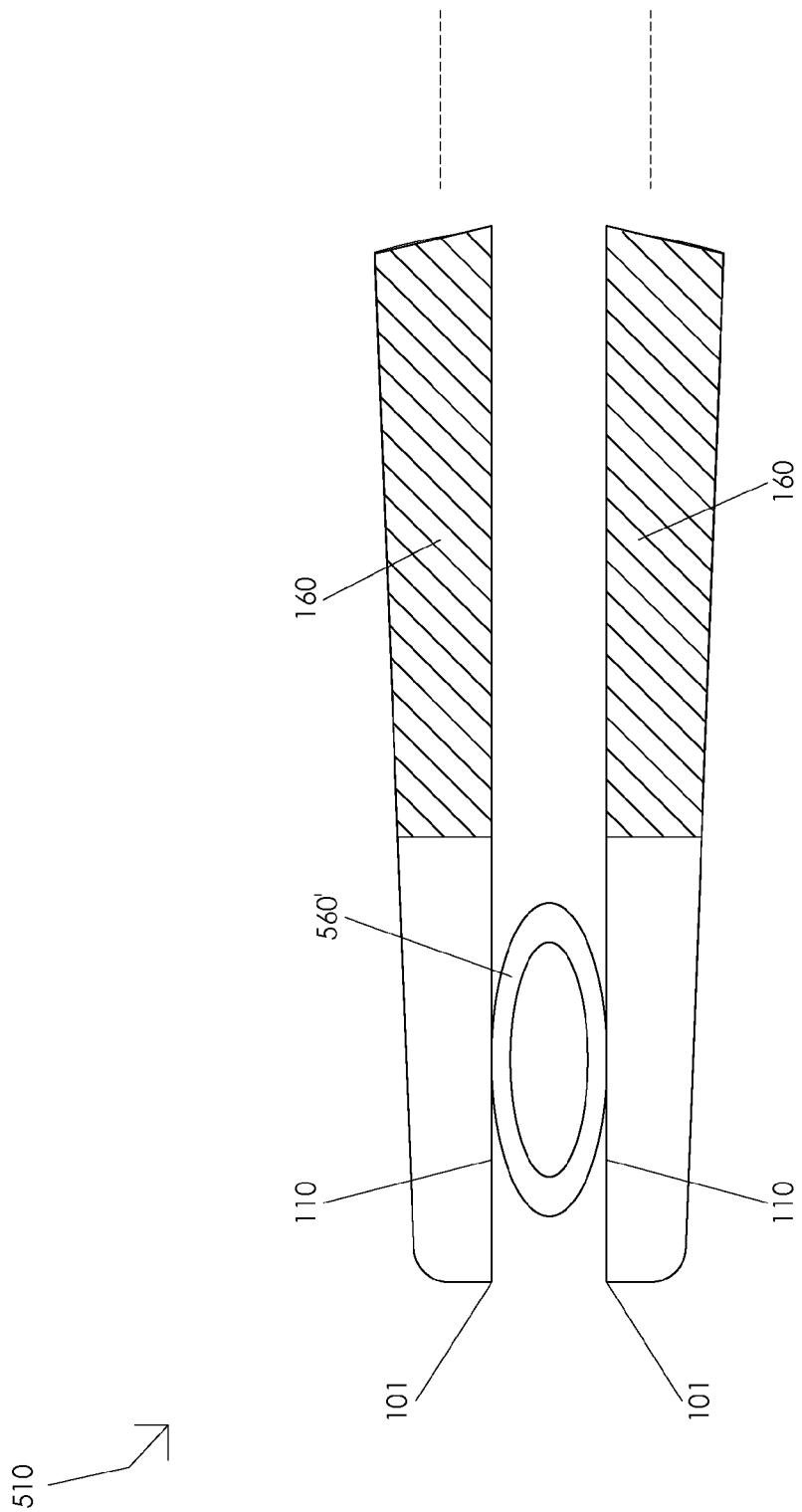
Figure 5C:
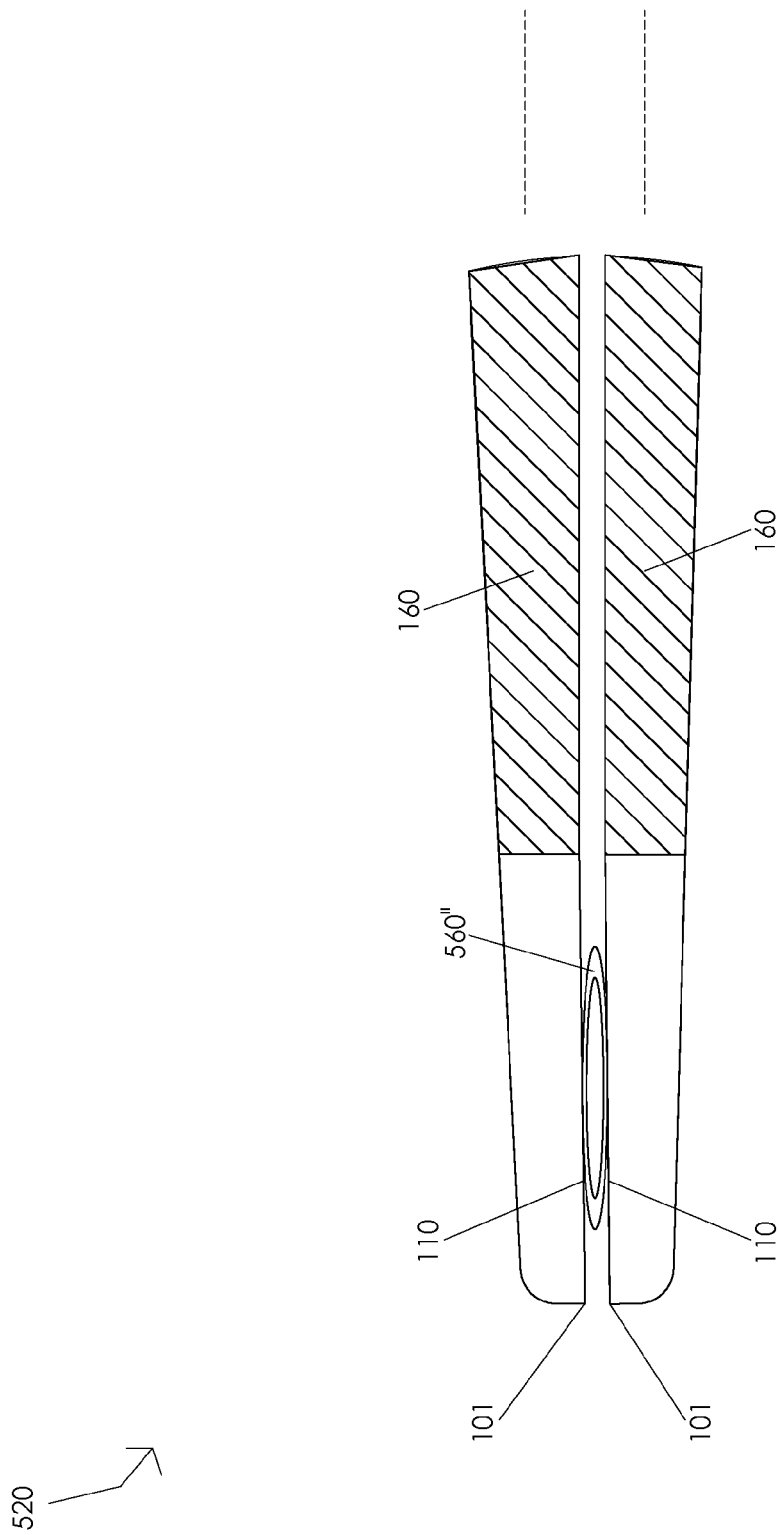

FIGS. 5A, 5B, and 5C are schematic diagrams illustrating a uniform compression of a vessel 560. In one or more embodiments, vessel 560 may comprise a blood vessel of an arteriovenous malformation. FIG. 5A illustrates an uncompressed vessel 500. Illustratively, vessel 560 may comprise an uncompressed vessel 500, e.g., when vessel 560 has a natural geometry. In one or more embodiments, vessel 560 may comprise an uncompressed vessel, e.g., when forceps jaws 160 comprise forceps jaws in a partially closed orientation 310. Illustratively, a surgeon may dispose vessel 560 between first forceps arm conductor tip 110 and second forceps arm conductor tip 110, e.g., when forceps jaws 160 comprise forceps jaws in an open orientation 300. In one or more embodiments, an application of a force to a lateral portion of forceps arms 100 may be configured to gradually close forceps jaws 160 from forceps jaws in an open orientation 300 to forceps jaws in a partially closed orientation 310. Illustratively, vessel 560 may electrically connect first forceps arm conductor tip 110 and second forceps arm conductor tip 110, e.g., when vessel 560 comprises an uncompressed vessel 500. In one or more embodiments, a surgeon may identify an orientation of forceps jaws 160 wherein conductor tips 110 initially contact vessel 560. Illustratively, a geometry of forceps arms 100 may be configured to allow a surgeon to visually identify an orientation of forceps jaws 160 wherein conductor tips 110 initially contact vessel 560. In one or more embodiments, a mass of forceps arms 100 may be configured to allow a surgeon to tactilely identify an orientation of forceps jaws 160 wherein conductor tips 110 initially contact vessel 560. Illustratively, a geometry of forceps arms 100 and a mass of forceps arms 100 may be configured to allow a surgeon to both visually and tactilely identify an orientation of forceps jaws 160 wherein conductor tips 110 initially contact vessel 560.

FIG. 5B illustrates a partially compressed vessel 510. Illustratively, an application of a force to a lateral portion of forceps arms 100 may be configured to uniformly compress vessel 560 from an uncompressed vessel 500 to a partially compressed vessel 510. In one or more embodiments, an application of a force to a lateral portion of forceps arms 100 may be configured to uniformly increase a contact area between vessel 560 and forceps arm conductor tips 110. Illustratively, vessel 560 may electrically connect first forceps arm conductor tip 110 and second forceps arm conductor tip 110, e.g., when vessel 560 comprises a partially compressed vessel 510. In one or more embodiments, an application of a force to a lateral portion of forceps arms 100 may be configured to compress vessel 560 wherein vessel 560 maintains a symmetrical geometry with respect to a medial axis of vessel 560. Illustratively, vessel 560 may have a symmetrical geometry with respect to a medial axis of vessel 560 when vessel 560 comprises a partially compressed vessel 510. In one or more embodiments, forceps jaws 160 may be configured to compress vessel 560 wherein no portion of vessel 560 is compressed substantially more than another portion of vessel 560, e.g., forceps jaws 160 may be configured to evenly compress vessel 560 without pinching a first portion of vessel 560 or bulging a second portion of vessel 560. Illustratively, vessel 560 may be evenly compressed when vessel 560 comprises a partially compressed vessel 510.

FIG. 5C illustrates a fully compressed vessel 520. Illustratively, an application of a force to a lateral portion of forceps arms 100 may be configured to uniformly compress vessel 560 from a partially compressed vessel 510 to a fully compressed vessel 520. In one or more embodiments, an application of a force to a lateral portion of forceps arms 100 may be configured to uniformly increase a contact area between vessel 560 and forceps arm conductor tips 110. Illustratively, vessel 560 may electrically connect first forceps arm conductor tip 110 and second forceps arm conductor tip 110, e.g., when vessel 560 comprises a fully compressed vessel 520. In one or more embodiments, a surgeon may uniformly cauterize vessel 560, e.g., when vessel 560 comprises a fully compressed vessel 520. Illustratively, a surgeon may uniformly achieve hemostasis of vessel 560, e.g., when vessel 560 comprises a fully compressed vessel 520. In one or more embodiments, an application of a force to a lateral portion of forceps arms 100 may be configured to compress vessel 560 wherein vessel 560 maintains a symmetrical geometry with respect to a medial axis of vessel 560. Illustratively, vessel 560 may have a symmetrical geometry with respect to a medial axis of vessel 560 when vessel 560 comprises a fully compressed vessel 520. In one or more embodiments, forceps jaws 160 may be configured to compress vessel 560 wherein no portion of vessel 560 is compressed substantially more than another portion of vessel 560, e.g., forceps jaws 160 may be configured to evenly compress vessel 560 without pinching a first portion of vessel 560 or bulging a second portion of vessel 560. Illustratively, vessel 560 may be evenly compressed when vessel 560 comprises a fully compressed vessel 520.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any system. Furthermore, while this description has been written in terms of a surgical instrument, the teachings of the present invention are equally suitable to any systems where the functionality may be employed. Therefore, it is the object of the appended claims to cover all such variations and modifications as come within the true spirit and scope of the invention.

What is claimed is:

1. An instrument comprising:
   a first forceps arm having a first forceps arm distal end and a first forceps arm proximal end;
   a first forceps arm grip of the first forceps arm having a first forceps arm grip distal end and a first forceps arm grip proximal end wherein the first forceps arm grip distal end is disposed between the first forceps arm distal end and the first forceps arm proximal end and wherein the first forceps arm grip proximal end is disposed between the first forceps arm distal end and the first forceps arm proximal end;
   a first superior incline angle of the first forceps arm grip, the first superior incline angle in a range of 150.0 to 170.0 degrees;
   a first inferior incline angle of the first forceps arm grip, the first inferior incline angle in a range of 15.0 to 30.0 degrees;
   a first forceps jaw of the first forceps arm having a first forceps jaw distal end and a first forceps jaw proximal end wherein the first forceps jaw distal end is the first forceps arm distal end and wherein the first forceps jaw proximal end is disposed between the first forceps arm grip distal end and the first forceps arm distal end;
   a first conductor tip of the first forceps arm having a first conductor tip distal end and a first conductor tip proximal end wherein the first conductor tip distal end is the first forceps arm distal end and the first forceps jaw distal end and wherein the first conductor tip proximal end is disposed between the first forceps jaw proximal end and the first forceps arm distal end;
   a first forceps arm aperture of the first forceps arm grip, the first forceps arm aperture having a first aperture perimeter length in range of 4.0 to 7.0 inches wherein the first forceps arm aperture is disposed between the first forceps arm grip distal end and the first forceps arm grip proximal end;
   a first input conductor housing of the first forceps arm;
   a first coating of an electrical insulator material over at least a portion of the first forceps arm;
   a second forceps arm having a second forceps arm distal end and a second forceps arm proximal end, the second forceps arm disposed opposite the first forceps arm;
   a second forceps arm grip of the second forceps arm having a second forceps arm grip distal end and a second forceps arm grip proximal end, the second forceps arm grip disposed opposite the first forceps arm grip wherein the second forceps arm grip distal end is disposed between the second forceps arm distal and the second forceps arm proximal end and wherein the second forceps arm grip proximal end is disposed between the second forceps arm distal end and the second forceps arm proximal end;
   a second superior incline angle of the second forceps arm grip, the second superior incline angle in a range of 150.0 to 170.0 degrees;
   a second inferior incline angle of the second forceps arm grip, the second inferior incline angle in a range of 15.0 to 30.0 degrees;
   a second forceps jaw of the second forceps arm having a second forceps jaw distal end and a second forceps jaw proximal end, the second forceps jaw disposed opposite the first forceps jaw wherein the second forceps jaw distal end is the second forceps arm distal end and wherein the second forceps jaw proximal end is disposed between the second forceps arm grip distal end and the second forceps arm distal end;
   a second conductor tip of the second forceps arm having a second conductor tip distal end and a second conductor tip proximal end, the second conductor tip disposed opposite the first conductor tip wherein the second conductor tip distal end is the second forceps arm distal end and the second forceps jaw distal end and wherein the second conductor tip proximal end is disposed between the second forceps jaw proximal end and the second forceps arm distal end;
   a second forceps arm aperture of the second forceps arm grip, the second forceps arm aperture having a second aperture perimeter length in range of 4.0 to 7.0 inches wherein the second forceps arm aperture is disposed between the second forceps arm grip distal end and the second forceps arm grip proximal end;
   a second input conductor housing of the second forceps arm;
   a second coating of the electrical insulator material over at least a portion of the second forceps arm; and
   an input conductor isolation mechanism configured to electrically isolate the first input conductor housing of the first forceps arm and the second input conductor housing of the second forceps arm wherein the first forceps arm proximal end is disposed in the input conductor isolation mechanism and the second forceps arm proximal end is disposed in the input conductor isolation mechanism.

2. The instrument of claim 1 further comprising:
   a first superior decline angle of the first forceps jaw, the first superior decline angle in a range of 5.0 to 15.0 degrees; and
   a second superior decline angle of the second forceps jaw, the second superior decline angle in a range of 5.0 to 15.0 degrees.

3. The instrument of claim 1 further comprising:
   a first inferior decline angle of the first forceps arm grip and the first forceps jaw, the first inferior decline angle in a range of 140.0 to 160.0 degrees; and
   a second inferior decline angle of the second forceps arm grip and the second forceps jaw, the second inferior decline angle in a range of 140.0 to 160.0 degrees.

4. An instrument comprising:
   a first forceps arm having a first forceps arm distal end and a first forceps arm proximal end;
   a first forceps arm grip of the first forceps arm having a first forceps arm grip distal end and a first forceps arm grip proximal end wherein the first forceps arm grip distal end is disposed between the first forceps arm distal end and the first forceps arm proximal end and wherein the first forceps arm grip proximal end is disposed between the first forceps arm distal end and the first forceps arm proximal end;
   a first forceps jaw of the first forceps arm having a first forceps jaw distal end and a first forceps jaw proximal end wherein the first forceps jaw distal end is the first forceps arm distal end and wherein the first forceps jaw proximal end is disposed between the first forceps arm grip distal end and the first forceps arm distal end;

a first superior decline angle of the first forceps jaw, the first superior decline angle in a range of 5.0 to 15.0 degrees;

a first inferior decline angle of the first forceps arm grip and the first forceps jaw, the first inferior decline angle in a range of 140.0 to 160.0 degrees;

a first conductor tip of the first forceps arm having a first conductor tip distal end and a first conductor tip proximal end wherein the first conductor tip distal end is the first forceps arm distal end and the first forceps jaw distal end and wherein the first conductor tip proximal end is disposed between the first forceps jaw proximal end and the first forceps arm distal end;

a first forceps arm aperture of the first forceps arm grip, the first forceps arm aperture having a first aperture perimeter length in range of 4.0 to 7.0 inches wherein the first forceps arm aperture is disposed between the first forceps arm grip distal end and the first forceps arm grip proximal end;

a first input conductor housing of the first forceps arm;

a first coating of an electrical insulator material over at least a portion of the first forceps arm;

a second forceps arm having a second forceps arm distal end and a second forceps arm proximal end, the second forceps arm disposed opposite the first forceps arm;

a second forceps arm grip of the second forceps arm having a second forceps arm grip distal end and a second forceps arm grip proximal end, the second forceps arm grip disposed opposite the first forceps arm grip wherein the second forceps arm grip distal end is disposed between the second forceps arm distal and the second forceps arm proximal end and wherein the second forceps arm grip proximal end is disposed between the second forceps arm distal end and the second forceps arm proximal end;

a second forceps jaw of the second forceps arm having a second forceps jaw distal end and a second forceps jaw proximal end, the second forceps jaw disposed opposite the first forceps jaw wherein the second forceps jaw distal end is the second forceps arm distal end and wherein the second forceps jaw proximal end is disposed between the second forceps arm grip distal end and the second forceps arm distal end;

a second superior decline angle of the second forceps jaw, the second superior decline angle in a range of 5.0 to 15.0 degrees;

a second inferior decline angle of the second forceps arm grip and the second forceps jaw, the second inferior decline angle in a range of 140.0 to 160.0 degrees;

a second conductor tip of the second forceps arm having a second conductor tip distal end and a second conductor tip proximal end, the second conductor tip disposed opposite the first conductor tip wherein the second conductor tip distal end is the second forceps arm distal end and the second forceps jaw distal end and wherein the second conductor tip proximal end is disposed between the second forceps jaw proximal end and the second forceps arm distal end;

a second forceps arm aperture of the second forceps arm grip, the second forceps arm aperture having a second aperture perimeter length in range of 4.0 to 7.0 inches wherein the second forceps arm aperture is disposed between the second forceps arm grip distal end and the second forceps arm grip proximal end;

a second input conductor housing of the second forceps arm;

a second coating of the electrical insulator material over at least a portion of the second forceps arm; and an input conductor isolation mechanism configured to electrically isolate the first input conductor housing of the first forceps arm and the second input conductor housing of the second forceps arm wherein the first forceps arm proximal end is disposed in the input conductor isolation mechanism and the second forceps arm proximal end is disposed in the input conductor isolation mechanism.

5. The instrument of claim 4 further comprising:

a first inferior incline angle of the first forceps arm grip, the first inferior incline angle in a range of 15.0 to 30.0 degrees; and a second superior incline angle of the second forceps arm grip, the second superior incline angle in a range of 150.0 to 170.0 degrees.

6. The instrument of claim 4 further comprising:

a first superior incline angle of the first forceps arm grip, the first superior incline angle in a range of 150.0 to 170.0 degrees; and a second inferior incline angle of the second forceps arm grip, the second inferior incline angle in a range of 15.0 to 30.0 degrees.

7. The instrument of claim 4 wherein the first forceps arm is manufactured from aluminum.

8. An instrument comprising:

a first forceps arm having a first forceps arm distal end and a first forceps arm proximal end;

a first forceps arm grip of the first forceps arm having a first forceps arm grip distal end and a first forceps arm grip proximal end wherein the first forceps arm grip distal end is disposed between the first forceps arm distal end and the first forceps arm proximal end and wherein the first forceps arm grip proximal end is disposed between the first forceps arm distal end and the first forceps arm proximal end;

a first forceps jaw of the first forceps arm having a first forceps jaw distal end and a first forceps jaw proximal end wherein the first forceps jaw distal end is the first forceps arm distal end and wherein the first forceps jaw proximal end is disposed between the first forceps arm grip distal end and the first forceps arm distal end;

a first conductor tip of the first forceps arm having a first conductor tip distal end and a first conductor tip proximal end wherein the first conductor tip distal end is the first forceps arm distal end and the first forceps jaw distal end and wherein the first conductor tip proximal end is disposed between the first forceps jaw proximal end and the first forceps arm distal end;

a first forceps arm aperture of the first forceps arm grip, the first forceps arm aperture having a first aperture perimeter length in range of 4.0 to 7.0 inches wherein the first forceps arm aperture is disposed between the first forceps arm grip distal end and the first forceps arm grip proximal end;

a first input conductor housing of the first forceps arm;

a first coating of an electrical insulator material over at least a portion of the first forceps arm;

a second forceps arm having a second forceps arm distal end and a second forceps arm proximal end, the second forceps arm disposed opposite the first forceps arm;

a second forceps arm grip of the second forceps arm having a second forceps arm grip distal end and a second forceps arm grip proximal end, the second forceps arm grip disposed opposite the first forceps arm grip wherein the second forceps arm grip distal end is disposed between the second forceps arm distal and the second forceps arm proximal end and wherein the second forceps arm grip proximal end is disposed between the second forceps arm distal end and the second forceps arm proximal end;

a second forceps jaw of the second forceps arm having a second forceps jaw distal end and a second forceps jaw proximal end, the second forceps jaw disposed opposite the first forceps jaw wherein the second forceps jaw distal end is the second forceps arm distal end and wherein the second forceps jaw proximal end is disposed between the second forceps arm grip distal end and the second forceps arm distal end;

a second conductor tip of the second forceps arm having a second conductor tip distal end and a second conductor tip proximal end, the second conductor tip disposed opposite the first conductor tip wherein the second conductor tip distal end is the second forceps arm distal end and the second forceps jaw distal end and wherein the second conductor tip proximal end is disposed between the second forceps jaw proximal end and the second forceps arm distal end;

a second input conductor housing of the second forceps arm;

a second coating of the electrical insulator material over at least a portion of the second forceps arm; and an input conductor isolation mechanism configured to electrically isolate the first input conductor housing of the first forceps arm and the second input conductor housing of the second forceps arm wherein the first forceps arm proximal end is disposed in the input conductor isolation mechanism and the second forceps arm proximal end is disposed in the input conductor isolation mechanism.

9. The instrument of claim 8 further comprising:

a second forceps arm aperture of the second forceps arm grip, the second forceps arm aperture having a second aperture perimeter length in range of 4.0 to 7.0 inches wherein the second forceps arm aperture is disposed between the second forceps arm grip distal end and the second forceps arm grip proximal end.

10. The instrument of claim 8 wherein the first coating of the electrical insulator material has a coating thickness in a range of 0.005 to 0.008 inches.

11. The instrument of claim 8 wherein the first forceps arm is manufactured from aluminum.

12. The instrument of claim 8 wherein the first forceps arm is manufactured from stainless steel.

13. The instrument of claim 8 wherein the first forceps arm is manufactured from a conductive polymer.

14. The instrument of claim 8 wherein the first forceps arm is manufactured from graphite.

15. The instrument of claim 8 wherein an application of a force to a lateral portion of the first forceps arm and a lateral portion of the second forceps arm is configured to cause a contact between the first forceps arm distal end and the second forceps arm distal end.

16. The instrument of claim 15 wherein the force has a magnitude in a range of 0.35 to 0.7 pounds.

17. The instrument of claim 16 wherein the first conductor tip proximal end is separated from the second conductor tip proximal end.

18. The instrument of claim 17 wherein the first conductor tip proximal end is separated from the second conductor tip proximal end by a distance in a range of 0.005 to 0.015 inches.

19. The instrument of claim 8 wherein the first forceps arm has a density in a range of 0.025 to 0.045 pounds per cubic inch.

20. The instrument of claim 8 wherein the first forceps arm has a surface area in a range of 4.5 to 7.5 square inches.

* * * * *